(12) United States Patent
Small et al.

(10) Patent No.: US 10,240,102 B2
(45) Date of Patent: Mar. 26, 2019

(54) LUBRICANT COMPOSITIONS CONTAINING HEXENE-BASED OLIGOMERS

(71) Applicant: Chevron Phillips Chemical Company LP, The Woodlands, TX (US)

(72) Inventors: Brooke L. Small, Kingwood, TX (US); Yemi Oyerinde, Houston, TX (US); Russell J. Bak, Kingwood, TX (US); Jeff C. Gee, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 176 days.

(21) Appl. No.: 15/460,305

(22) Filed: Mar. 16, 2017

(65) Prior Publication Data

US 2018/0265799 A1    Sep. 20, 2018

(51) Int. Cl.
| | |
|---|---|
| C10M 105/04 | (2006.01) |
| C10M 107/10 | (2006.01) |
| C10M 171/02 | (2006.01) |
| C07C 9/15 | (2006.01) |
| C07C 9/22 | (2006.01) |

(52) U.S. Cl.
CPC ............. *C10M 105/04* (2013.01); *C07C 9/15* (2013.01); *C07C 9/22* (2013.01); *C10M 107/10* (2013.01); *C10M 171/02* (2013.01); C10M 2203/022 (2013.01); C10M 2203/024 (2013.01); C10M 2205/0285 (2013.01); C10N 2220/022 (2013.01); C10N 2230/02 (2013.01); C10N 2270/00 (2013.01)

(58) Field of Classification Search
CPC ............. C10M 105/04; C10M 107/10; C10M 171/02; C10M 2205/0285; C10M 2203/022; C10M 2203/024; C07C 9/15; C07C 9/22; C10N 2270/00; C10N 2230/02; C10N 2220/022
See application file for complete search history.

(56) References Cited

U.S. PATENT DOCUMENTS

| | | |
|---|---|---|
| 1,815,022 A | 7/1931 | Davis |
| 2,015,748 A | 10/1935 | Frolich |
| 2,191,498 A | 2/1940 | Reiff |
| 2,387,501 A | 10/1945 | Dietrich |
| 2,443,264 A | 6/1948 | Mikeska |
| 2,655,479 A | 1/1949 | Munday et al. |
| 2,471,115 A | 5/1949 | Mikeska |
| 2,526,497 A | 10/1950 | Mikeska |
| 2,591,577 A | 1/1952 | McDermott |
| 2,666,746 A | 1/1954 | Munday et al. |
| 2,719,125 A | 9/1955 | Roberts |
| 2,719,126 A | 9/1955 | Fields et al. |
| 2,721,877 A | 10/1955 | Popkin et al. |
| 2,721,878 A | 10/1955 | Popkin |
| 3,036,003 A | 5/1962 | Verdol et al. |
| 3,087,932 A | 4/1963 | Little, Jr. |
| 3,087,936 A | 4/1963 | Le Suer et al. |
| 3,172,892 A | 3/1965 | Le Suer et al. |
| 3,200,107 A | 8/1965 | Le Suer et al. |
| 3,215,707 A | 11/1965 | Rense |
| 3,219,666 A | 11/1965 | Norman et al. |
| 3,242,099 A | 3/1966 | Manyik et al. |
| 3,250,715 A | 5/1966 | Wyman |
| 3,254,025 A | 5/1966 | Le Suer et al. |
| 3,272,746 A | 9/1966 | Le Suer et al. |
| 3,275,554 A | 9/1966 | Wagenaar |
| 3,316,177 A | 4/1967 | Dorer, Jr. |
| 3,322,670 A | 5/1967 | Burt et al. |
| 3,329,658 A | 7/1967 | Fields |
| 3,341,542 A | 9/1967 | Le Suer et al. |
| 3,413,347 A | 11/1968 | Worrel |
| 3,438,757 A | 4/1969 | Honnen et al. |
| 3,444,170 A | 5/1969 | Norman et al. |
| 3,449,250 A | 6/1969 | Fields |
| 3,454,555 A | 7/1969 | van der Voort et al. |
| 3,454,607 A | 7/1969 | Le Suer et al. |
| 3,519,565 A | 7/1970 | Coleman |
| 3,541,012 A | 11/1970 | Stuebe |
| 3,565,804 A | 2/1971 | Honnen et al. |
| 3,630,904 A | 12/1971 | Musser et al. |
| 3,632,511 A | 1/1972 | Liao |
| 3,652,616 A | 3/1972 | Watson et al. |
| 3,666,730 A | 5/1972 | Coleman |
| 3,687,849 A | 8/1972 | Abbott |
| 3,697,574 A | 10/1972 | Piasek et al. |

(Continued)

FOREIGN PATENT DOCUMENTS

| | | | |
|---|---|---|---|
| WO | WO 2007/011459 | 1/2007 | |
| WO | WO-2018170110 A1 * | 9/2018 | .......... C10M 105/04 |

OTHER PUBLICATIONS

International Search Report and Written Opinion for PCT/US2018/022404 dated Jun. 22, 2018.

*Primary Examiner* — Pamela H Weiss
(74) *Attorney, Agent, or Firm* — Merchant & Gould P.C.

(57) ABSTRACT

Disclosed herein are oligomerization processes using feedstocks containing 1-hexene to produce an oligomer product, and methods for recovering a heavy 1-hexene oligomer from the oligomer product and hydrogenating the heavy 1-hexene oligomer. The resultant hydrogenated heavy 1-hexene oligomer can be blended with other PAO's to form 100 cSt and 40 cSt lubricant compositions, which have viscosity index and pour point properties that are equivalent to or better than respective 100 cSt and 40 cSt 1-decene PAO's.

16 Claims, No Drawings

(56) References Cited

U.S. PATENT DOCUMENTS

| | | | |
|---|---|---|---|
| 3,702,300 A | 11/1972 | Coleman | |
| 3,703,536 A | 11/1972 | Piasek et al. | |
| 3,704,308 A | 11/1972 | Piasek et al. | |
| 3,725,277 A | 4/1973 | Worrel | |
| 3,725,480 A | 4/1973 | Traise et al. | |
| 3,726,882 A | 4/1973 | Traise et al. | |
| 3,751,365 A | 8/1973 | Piasek et al. | |
| 3,755,433 A | 8/1973 | Miller et al. | |
| 3,756,953 A | 9/1973 | Piasek et al. | |
| 3,770,854 A | 11/1973 | Morris et al. | |
| 3,787,374 A | 1/1974 | Adams | |
| 3,798,165 A | 3/1974 | Piasek et al. | |
| 3,803,039 A | 4/1974 | Piasek et al. | |
| 3,822,209 A | 7/1974 | Knapp et al. | |
| 3,948,800 A | 4/1976 | Meinhardt | |
| 4,100,082 A | 7/1978 | Clason et al. | |
| 4,234,435 A | 11/1980 | Meinhardt et al. | |
| 4,426,305 A | 1/1984 | Malec | |
| 4,434,309 A * | 2/1984 | Larkin | C07O 2/20 585/10 |
| 4,454,059 A | 6/1984 | Pindar et al. | |
| 4,501,678 A | 2/1985 | Katayama et al. | |
| 4,767,551 A | 8/1988 | Hunt et al. | |
| 4,794,096 A | 12/1988 | Ewen | |
| 4,798,684 A | 1/1989 | Salomon | |
| 4,808,561 A | 2/1989 | Welborn, Jr. | |
| 4,827,064 A | 5/1989 | Wu | |
| 4,827,073 A * | 5/1989 | Wu | C10G 50/02 502/305 |
| 4,941,984 A | 7/1990 | Chamberlin, III et al. | |
| 5,034,141 A | 7/1991 | Habeeb | |
| 5,034,142 A | 7/1991 | Beltzer | |
| 5,084,197 A | 1/1992 | Galic | |
| 5,576,259 A | 11/1996 | Hasegawa et al. | |
| 5,693,598 A | 12/1997 | Abraham et al. | |
| 5,705,458 A | 1/1998 | Roby et al. | |
| 5,807,938 A | 9/1998 | Kaneko et al. | |
| 5,919,983 A | 7/1999 | Rosen et al. | |
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 7,026,494 B1 | 4/2006 | Yang et al. | |
| 7,041,617 B2 | 5/2006 | Jensen et al. | |
| 7,199,073 B2 | 4/2007 | Martin et al. | |
| 7,226,886 B2 | 6/2007 | Jayaratne et al. | |
| 7,294,599 B2 | 11/2007 | Jensen et al. | |
| 7,312,283 B2 | 12/2007 | Martin et al. | |
| 7,517,939 B2 | 4/2009 | Yang et al. | |
| 7,547,811 B2 * | 6/2009 | Kramer | C10G 50/02 585/510 |
| 7,601,665 B2 | 10/2009 | McDaniel et al. | |
| 7,619,047 B2 | 11/2009 | Yang et al. | |
| 7,884,163 B2 | 2/2011 | McDaniel et al. | |
| 7,919,639 B2 | 4/2011 | Murray et al. | |
| 8,080,681 B2 | 12/2011 | Murray et al. | |
| 8,114,946 B2 | 2/2012 | Yang et al. | |
| 8,309,485 B2 | 11/2012 | Yang et al. | |
| 8,530,712 B2 | 9/2013 | Wu et al. | |
| 8,623,973 B1 | 1/2014 | McDaniel et al. | |
| 8,703,886 B1 | 4/2014 | Yang et al. | |
| 8,921,291 B2 | 12/2014 | Wu et al. | |
| 9,023,959 B2 | 5/2015 | McDaniel et al. | |
| 2009/0005279 A1 | 1/2009 | Wu et al. | |
| 2009/0116771 A1 * | 5/2009 | Kamimura | C10M 107/02 384/100 |
| 2010/0292424 A1 | 11/2010 | Wu et al. | |
| 2010/0317904 A1 | 12/2010 | Small et al. | |
| 2013/0172498 A1 | 7/2013 | Hlavinka et al. | |

* cited by examiner

LUBRICANT COMPOSITIONS CONTAINING HEXENE-BASED OLIGOMERS

BACKGROUND OF THE INVENTION

The present invention relates generally to processes for oligomerizing 1-hexene with a catalyst system containing a metallocene compound, a chemically-treated solid oxide, and an optional organoaluminum compound, to 1-hexene oligomers having specific viscosity index and pour point characteristics, and to base oil and lubricant compositions containing the 1-hexene oligomers.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Hydrogenated oligomer compositions are disclosed and described herein. A hydrogenated oligomer composition in one embodiment of this invention can comprise at least 80 wt. % monomer units derived from 1-hexene, and can be characterized by a 100° C. kinematic viscosity in a range from 75 to 150 cSt, a viscosity index in a range from 150 to 180, and a pour point in a range from −20 to −40° C. A hydrogenated oligomer composition in another embodiment of this invention can comprise at least 95 wt. % monomer units derived from 1-hexene, and can be characterized by a 100° C. kinematic viscosity in a range from 80 to 125 cSt, a viscosity index in a range from 150 to 170, and a pour point in a range from −25 to −40° C. A hydrogenated oligomer composition in yet another embodiment of this invention can comprise at least 98 wt. % monomer units derived from 1-hexene, and can be characterized by a 100° C. kinematic viscosity in a range from 85 to 115 cSt, a viscosity index in a range from 155 to 165, and a pour point in a range from −25 to −35° C.

The hydrogenated oligomer compositions can be used in base oils, or in lubricants and other compositions. In an embodiment, a base oil composition (or a lubricant composition) having a 100° C. kinematic viscosity in a range from 30 to 50 cSt is provided, and in this embodiment, the base oil composition (or the lubricant composition) can comprise (i) any of the hydrogenated oligomer compositions disclosed herein, and (ii) a low viscosity polyalphaolefin (PAO is used herein as an abbreviation for polyalphaolefin) having a 100° C. kinematic viscosity in a range from 1 to 20 cSt. The weight ratio of the hydrogenated oligomer composition:low viscosity PAO often can be in a range from 25:75 to 90:10.

In another embodiment, a base oil composition (or a lubricant composition) having a 100° C. kinematic viscosity in a range from 80 to 120 cSt is provided, and in this embodiment, the base oil composition (or the lubricant composition) can comprise (i) any of the hydrogenated oligomer compositions disclosed herein, and (ii) a high viscosity PAO having a 100° C. kinematic viscosity in a range from 75 to 150 cSt. The weight ratio of the hydrogenated oligomer composition:high viscosity PAO often can be in a range from 25:75 to 80:20.

Both the foregoing summary and the following detailed description, including examples, are explanatory only. Accordingly, the foregoing summary and the following detailed description should not be considered to be restrictive. Further, features or variations can be provided in addition to those set forth herein. For example, certain aspects and embodiments can be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features, aspects, and/or embodiments can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a product stream consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a catalyst system consistent with certain embodiments of the present invention can comprise; alternatively, consist essentially of; or alternatively, consist of; a metallocene compound, a chemically-treated solid oxide, and an organoaluminum compound.

The terms "a," "an," and "the" are intended to include plural alternatives, e.g., at least one, unless otherwise specified. For instance, and not to be limiting, the disclosure of "an additive" or "a separation step" is meant to encompass one, or combinations of more than one, additive or separation step (e.g., a flash process, a distillation process, etc.), respectively, unless otherwise specified. Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, and not to be limiting, a general reference to hexene (or hexenes) includes all linear or branched, acyclic or cyclic, hydrocarbon compounds having six carbon atoms and 1 carbon-carbon double bond; a general reference to pentane includes n-pentane, 2-methylbutane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans, trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The terms "contact product," "contacting," and the like, are used herein to describe compositions and methods wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The terms "oligomerization product" and "oligomer product" include all products made by the "oligomerization" process including the "oligomers" and products which are not "oligomers" (e.g., polymer). As used herein, "heavy oligomer product" typically refers to a 1-hexene oligomer (or composition) having little to no light 1-hexene oligomers, e.g., a composition where at least a portion of unreacted 1-hexene and at least a portion of light 1-hexene oligomers (such as $C_{12}$ to $C_{24}$, $C_{12}$ to $C_{30}$, or $C_{12}$ to $C_{36}$ oligomers), if produced, have been removed from the "oligomer product." As used herein, "hydrogenated oligomer composition" typically refers to a composition having little to no hydrogenated 1-hexene and light 1-hexene oligomers, e.g., a composition where the quantity of hydrogenated light 1-hexene oligomers (such as $C_{12}$ to $C_{24}$, $C_{12}$ to $C_{30}$, or $C_{12}$ to $C_{36}$ hydrogenated oligomers) are less than a prescribed value. The heavy oligomer product generally refers to a composition prior to hydrogenation, while hydrogenated oligomer composition generally refers to an oligomer composition after hydrogenation. These terms also can be used generically herein to include 1-hexene homo-oligomers and/or 1-hexene co-oligomers, and hydrogenated 1-hexene homo-oligomers and/or hydrogenated 1-hexene co-oligomers.

As utilized herein "olefin feedstock" refers to material which is oligomerized while "monomer" or "monomer units" refers to the olefin feedstock incorporated into the oligomer, oligomer product, heavy oligomer product, hydrogenated oligomer composition, or "polyalphaolefin" (PAO). However, "monomer" can be used synonymously with "olefin feedstock" without detracting from the disclosure.

A "polyalphaolefin" (PAO) is a mixture of hydrogenated (or alternatively, substantially saturated) oligomers, containing units derived from an alpha olefin monomer(s). Unless specified otherwise, the PAO can contain units derived from alpha olefin monomer units, which can be the same (hydrogenated or substantially saturated alpha olefin homo-oligomer) or can be different (hydrogenated or substantially saturated alpha olefin co-oligomer). Generally, the alpha olefin monomer utilized to produce the polyalphaolefin can be any alpha olefin monomer described herein. One having ordinary skill in the art would recognize that the process(es) for producing the PAO can leave some hydrogenated monomer in the PAO (e.g., less than 1 wt. % based on the total amount of the PAO), and this quantity of hydrogenated monomer can be specified.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Oligomerizations of feedstocks containing 1-hexene using a metallocene-based catalyst system containing a chemically-treated solid oxide are disclosed herein. Also disclosed herein are 1-hexene oligomer compositions or hydrogenated 1-hexene oligomer compositions that can be blended with other PAO's to form 100 cSt and 40 cSt lubricant compositions, which have properties (e.g., viscosity index and pour point) that are equivalent to or better than respective 100 cSt and 40 cSt 1-decene PAO's.

1-Hexene Oligomers

An illustrative and non-limiting example of a hydrogenated oligomer composition consistent with the present invention can comprise at least 80 wt. % monomer units derived from 1-hexene, and can be characterized by a 100° C. kinematic viscosity in a range from 75 to 150 cSt, a viscosity index in a range from 150 to 180, and a pour point in a range from −20 to −40° C. Another illustrative and non-limiting example of a hydrogenated oligomer composition consistent with the present invention can comprise at least 95 wt. % monomer units derived from 1-hexene, and can be characterized by a 100° C. kinematic viscosity in a range from 80 to 125 cSt, a viscosity index in a range from 150 to 170, and a pour point in a range from −25 to −40° C. Yet another illustrative and non-limiting example of a hydrogenated oligomer composition consistent with the present invention can comprise at least 98 wt. % monomer units derived from 1-hexene, and can be characterized by a 100° C. kinematic viscosity in a range from 85 to 115 cSt, a viscosity index in a range from 155 to 165, and a pour point in a range from −25 to −35° C. These illustrative and non-limiting examples of hydrogenated oligomer compositions consistent with the present invention also can have any of the characteristics or properties of the hydrogenated oligomer compositions provided herein, and in any combination.

The pour point of the hydrogenated oligomer composition typically can fall within a range from −20 to −40° C. For instance, the minimum pour point of the hydrogenated oligomer composition can be −40, −38, −36, or −35° C.; alternatively, or additionally, the maximum pour point can be −20, −22, −25, or −28° C. Generally, the pour point of the hydrogenated oligomer composition can be in a range from any minimum pour point temperature disclosed herein to any maximum pour point temperature disclosed herein. Therefore, suitable non-limiting ranges for the pour point of the hydrogenated oligomer composition can include the following ranges: from −20 to −40° C., from −20 to −38° C., from −20 to −35° C., from −22 to −38° C., from −22 to −36° C., from −25 to −40° C., from −25 to −35° C., or from −28 to −40° C. Other appropriate ranges for the pour point of the hydrogenated oligomer composition are readily apparent from this disclosure. Generally, the pour point of the hydrogenated oligomer composition can be measured using ASTM D97-04.

The hydrogenated oligomer composition can have a viscosity index of from 150 to 180. For instance, the minimum viscosity index of the hydrogenated oligomer composition can be at least 150, 152, 155, or 157; alternatively, or additionally, the maximum viscosity index can be 180, 175, 170, or 165. Generally, the viscosity index of the hydrogenated oligomer composition can be in a range from any minimum viscosity index disclosed herein to any maximum viscosity index disclosed herein. Therefore, suitable non-limiting ranges for the viscosity index of the hydrogenated oligomer composition can include the following ranges: from 150 to 180, from 150 to 175, from 150 to 170, from 150 to 165, from 152 to 175, from 152 to 170, from 155 to 175, from 155 to 165, from 157 to 175, or from 157 to 165. Other appropriate ranges for the viscosity index of the hydrogenated oligomer composition are readily apparent from this disclosure. Generally, the viscosity index of the hydrogenated oligomer composition can be measured using ASTM D7042-04.

Consistent with embodiments of this invention, the hydrogenated oligomer composition can have a 40° C. kinematic viscosity ranging from 750 to 2800 cSt. For instance, the hydrogenated oligomer composition can have a minimum 40° C. kinematic viscosity of 750, 900, 1000, 1100, 1200, or 1300 cSt; alternatively, or additionally, the maximum 40° C. kinematic viscosity of the hydrogenated oligomer composition can be 2800, 2500, 2000, 1800, 1600, or 1500 cSt. Generally, the 40° C. kinematic viscosity of the hydrogenated oligomer composition can be in a range from any minimum kinematic viscosity disclosed herein to any maximum kinematic viscosity disclosed herein. Therefore, suitable non-limiting ranges for the 40° C. kinematic viscosity of the hydrogenated oligomer composition can include the following ranges: from 750 to 2800 cSt, from 900 to 2500 cSt, from 900 to 1800 cSt, from 1000 to 2500 cSt, from 1000 to 2000 cSt, from 1000 to 1500 cSt, from 1100 to 1800 cSt, from 1200 to 2000 cSt, from 1200 to 1800 cSt, from 1200 to 1600 cSt, from 1200 to 1500 cSt, from 1300 to 2800 cSt, from 1300 to 2000 cSt, or from 1300 to 1500 cSt. Other appropriate ranges for the 40° C. kinematic viscosity of the hydrogenated oligomer composition are readily apparent from this disclosure.

The hydrogenated oligomer composition can have a 100° C. kinematic viscosity ranging from 75 to 150 cSt. For instance, the hydrogenated oligomer composition can have a minimum 100° C. kinematic viscosity of 75, 80, 85, 90, or 95 cSt; alternatively, or additionally, the maximum 100° C. kinematic viscosity of the hydrogenated oligomer composition can be 150, 140, 125, 115, or 110 cSt. Generally, the 100° C. kinematic viscosity of the hydrogenated oligomer composition can be in a range from any minimum kinematic viscosity disclosed herein to any maximum kinematic viscosity disclosed herein. Therefore, suitable non-limiting ranges for the 100° C. kinematic viscosity of the hydrogenated oligomer composition can include the following ranges: from 75 to 150 cSt, from 75 to 125 cSt, from 80 to 140 cSt, from 80 to 125 cSt, from 85 to 140 cSt, from 85 to 125 cSt, from 85 to 115 cSt, from 90 to 150 cSt, from 90 to 125 cSt, from 90 to 110 cSt, from 95 to 140 cSt, from 95 to 125 cSt, or from 95 to 115 cSt. Other appropriate ranges for the 100° C. kinematic viscosity of the hydrogenated oligomer composition are readily apparent from this disclosure. Generally, the viscosities of the hydrogenated oligomer composition can be measured using ASTM D7042-04 or ASTM D445-06.

In embodiments of this invention, the hydrogenated oligomer compositions can contain predominantly 1-hexene monomer units. Generally, the hydrogenated oligomer composition comprises at least 80 wt. % monomer units derived from 1-hexene. In some embodiments, the hydrogenated oligomer composition can contain at least 85 wt. % 1-hexene units, at least 90 wt. % 1-hexene units, at least 95 wt. % 1-hexene units, at least 97 wt. % 1-hexene units, at least 98 wt. % 1-hexene units, at least 98.5 wt. % 1-hexene units, or at least 99 wt. % 1-hexene units. In a further embodiment, the hydrogenated oligomer composition can contain at least 99.5 wt. % 1-hexene units.

Generally, the hydrogenated oligomer composition contains very little, if any, hydrogenated oligomers having 24 carbon atoms or less, 30 carbon atoms or less, or 36 carbon atoms or less. In an embodiment, the hydrogenated oligomer composition can contain less than 5 wt. %, less than 4 wt. %, less than 3 wt. %, less than 2 wt. %, less than 1.5 wt. %, less than 1 wt. %, less than 0.75 wt. %, less than 0.5 wt. %, less than 0.25 wt. %, or less than 0.1 wt. % hydrogenated oligomers having 24 carbon atoms or less, 30 carbon atoms or less, or 36 carbon atoms or less.

The hydrogenated oligomer composition can be a liquid 1-hexene oligomer at ambient conditions in particular embodiments of this invention. Thus, the hydrogenated oligomer composition can be a liquid (not a solid or gas) at 25° C. and 1 atmosphere (101.3 kPa) pressure.

In an embodiment, the hydrogenated oligomer compositions can have "no discernable crystallization" above −40° C. according to differential scanning calorimetry (abbreviated DSC; ASTM D3418-97). While referred to as a crystallization, the term also encompasses a discernable melting as determined by thermal analysis using a differential scanning calorimeter (DSC). The hydrogenated oligomer composition has "no discernable crystallization" if the melting enthalpy (ΔH) of the sample (in grams) in a second heat scan is less than 1.5 J/g. In some instances, the melting enthalpy can be less than 1.0 J/g, or less than 0.5 J/g. The sample is cooled to −60° C. and held at −60° C. for 5 minutes before each heating scan. The first heating scan and second heating scan are conducted with a heating rate of 10° C./min from −60° C. to 100° C. The interceding cooling scan is conducted at rate of 10° C./min from 100° C. to −60° C. The DSC test is performed using a flow rate of 20 cc/min of nitrogen. The crystallization temperature (if present) or melting temperature (if present), and crystallization enthalpy (if present) or melting enthalpy (if present), is taken to be the temperature and enthalpy of the DSC crystallization transition or DSC melting transition, respectively, of the second heating scan and can be represented by an endotherm or an exotherm.

Oligomerization Processes

Embodiments of this invention are directed to oligomerization processes for oligomerizing an olefin feedstock containing predominately 1-hexene, the production of an oligomer product, the recovery of a heavy oligomer product, and the formation of a hydrogenated oligomer composition, whose typical properties are disclosed herein. A representative process can comprise (or consist essentially of, or consist of) (a) contacting an olefin feedstock comprising at least 80 wt. % 1-hexene with a catalyst system comprising (i) a metallocene compound, (ii) a chemically-treated solid oxide, and (iii) optionally, an organoaluminum compound; (b) forming an oligomer product under oligomerization conditions; (c) isolating a heavy oligomer product by removing at least a portion of unreacted 1-hexene and light 1-hexene oligomers from the oligomer product using one or more separations steps; and (d) hydrogenating the heavy oligomer product to produce a hydrogenated oligomer composition.

Generally, the features of the processes (e.g., the olefin feedstock, the catalyst system, the metallocene compound, the chemically-treated solid oxide, the organoaluminum compound, the materials comprising and/or features of the oligomer product, the oligomerization conditions under which the oligomer product is formed, the materials comprising and/or features of the heavy oligomer product, the light 1-hexene oligomers, the separations steps, and the materials comprising and/or features of the hydrogenated oligomer composition, among others) are independently described herein, and these features can be combined in any combination to further describe the disclosed processes. Moreover, additional process steps can be performed before, during, and/or after any of the steps of any of the processes disclosed herein, unless stated otherwise.

The olefin feedstock comprising 1-hexene can come from many different sources and have a wide range of compositional attributes. Generally, however, the olefin feedstock can contain at least 80 wt. % 1-hexene. In some embodiments, the olefin feedstock can contain at least 85 wt. % 1-hexene, at least 90 wt. % 1-hexene, or at least 95 wt. % 1-hexene, while in other embodiments, the olefin feedstock can contain at least 97 wt. % 1-hexene, at least 98 wt. % 1-hexene, at least 98.5 wt. % 1-hexene, or at least 99 wt. % 1-hexene. In a further embodiment, the olefin feedstock can contain at least 99.5 wt. % 1-hexene.

The oligomerization conditions can comprise any suitable oligomerization temperature. For example, the oligomerization temperature can be in a range from 0° C. to 165° C. In an embodiment, the minimum oligomerization temperature can be 0, 20, 35, 40, 45, or 50° C.; alternatively, or additionally, the maximum oligomerization temperature can be 165, 160, 150, 140, 130, 100, 80, 75, or 70° C. Generally, the oligomerization temperature can be in a range from any minimum oligomerization temperature disclosed herein to any maximum oligomerization temperature disclosed herein. Therefore, in some embodiments, the oligomerization temperature can be in a range from 20° C. to 160° C., from 40° C. to 160° C., or from 40° C. to 150° C., while in other embodiments, the oligomerization temperature can be in a range from 50° C. to 150° C., from 50° C. to 140° C., or from 50° C. to 130° C. Yet, in further embodiments, the oligomerization temperature can be in a range from 20° C. to 100° C., from 20° C. to 80° C., from 35° C. to 75° C., from 40° C. to 70° C., or from 45° C. to 70° C. Other appropriate oligomerization temperatures and temperature ranges are readily apparent from this disclosure.

The oligomerization conditions can comprise any suitable reaction pressure, and typically falls within a range from atmospheric pressure to 2,000 psig (13.8 MPa). For instance, the minimum reaction pressure can be atmospheric pressure, 16 psia (110 kPa), 20 psia (138 kPa), 25 psia (172 kPa), 50 psia (344 kPa), 100 psia (689 kPa), 150 psia (1.0 MPa), 200 psig (1.4 MPa), or 250 psig (1.5 MPa); alternatively, or additionally, the maximum reaction pressure can be 2,000 psia (13.8 MPa), 1,500 psia (10.3 MPa), 1250 psia (8.6 MPa), 1000 psia (6.9 MPa), 750 psia (5.2 MPa), or 500 psia (3.4 MPa). Generally, the reaction pressure can be in a range from any minimum reaction pressure disclosed herein to any maximum reaction pressure disclosed herein. Therefore, suitable non-limiting ranges for the reaction pressure can include the following ranges: from atmospheric pressure to 2,000 psig (13.8 MPa), from 20 psia (138 kPa) to 2,000 psig (1.7 MPa), from atmospheric pressure to 1000 psig (6.9 MPa), from 25 psia (172 kPa) to 1000 psia (6.9 MPa), from atmospheric pressure to 750 psia (5.2 MPa), from 20 psia (138 kPa) to 750 psia (5.2 MPa), or from atmospheric pressure to 500 psig (3.4 MPa). Other appropriate reaction pressures are readily apparent from this disclosure.

In some embodiments, the oligomer product can be formed in the substantial absence of added hydrogen. In these embodiments, no hydrogen is added to the oligomerization reaction system. As one of ordinary skill in the art would recognize, hydrogen can be generated in-situ by metallocene catalyst systems in various olefin oligomerization processes, and the amount generated can vary depending upon the specific catalyst system and metallocene compound employed, the type of oligomerization process used, the oligomerization reaction conditions utilized, and so forth. As used herein, the substantial absence of added hydrogen can refer to the situation where less than 1 psig (6.9 kPa), 0.75 psi (5.1 kPa), 0.5 psig (3.4 kPa), 0.25 psig (1.7 kPa), or 0.1 psig (0.69 kPa) is added to the olefin oligomerization process.

In other embodiments, it may be desirable to conduct the oligomerization process in the presence of a certain amount of added hydrogen, for instance, to reduce molecular weight, to reduce viscosity, etc. Accordingly, in these embodiments, the oligomer product can be formed in the presence of hydrogen, i.e., the olefin feedstock (containing 1-hexene), the catalyst system, and hydrogen can be contacted to form the oligomer product under oligomerization conditions. For instance, the minimum hydrogen partial pressure can be 1 psig (6.9 kPa), 5 psig (34 kPa), 10 psig (69 kPa), or 25 psig (172 kPa); alternatively, or additionally, the maximum hydrogen partial pressure can be 2000 psig (13.8 MPa), 1500 psig (10.3 MPa), 1000 psig (6.9 MPa), or 500 psig (3.5 MPa). Generally, the oligomer product can be formed at a hydrogen partial pressure in a range from any minimum hydrogen partial pressure disclosed herein to any maximum hydrogen partial pressure disclosed herein. Therefore, suitable non-limiting ranges for the hydrogen partial pressure can include the following ranges: from 1 psig (6.9 kPa) to 2000 psig (13.8 MPa), from 5 psig (34 kPa) to 1500 psig (10.3 MPa), from 10 psig (69 kPa) to 1000 psig (6.9 MPa), from 10 psig (69 kPa) to 500 psig (3.5 MPa), or from 25 psig (172 kPa) to 500 psig (3.4 MPa). Other appropriate hydrogen partial pressures are readily apparent from this disclosure.

Any suitable reactor or vessel within an oligomerization reaction system can be used to form the oligomer product, non-limiting examples of which can include a fixed bed reactor, a stirred tank reactor, a plug flow reactor, and a loop slurry reactor, including more than one reactor in series or in parallel, and including any combination of reactor types and arrangements. In one embodiment, the reaction system can comprise a single reactor (e.g., a single loop slurry rector or a single stirred tank reactor), while in another embodiment, the reaction system can comprise two reactors in series (or parallel).

In the processes described herein, the catalyst system can be deactivated. Deactivating the catalyst system can comprise contacting the oligomer product with a suitable catalyst system deactivating agent, or subjecting the oligomer product to suitable process steps to deactivate the catalyst system, or a combination of both. The catalyst system deactivating agent can comprise (or consist essentially of, or consist of) water, an alcohol compound, an amine compound, or any combination thereof; alternatively, water; alternatively, an alcohol compound; or alternatively, an amine compound. In an embodiment, the alcohol compound can be a monoalcohol compound, a diol compound, a polyol compound, or any combination thereof. In some embodiments, the alcohol compound can comprise, consist essentially of, or consist of, a $C_1$ to $C_{20}$ mono alcohol. In some embodiments, the alcohol compound can comprise, consist essentially of, or consist of, methanol, ethanol, a propanol, a butanol, a pentanol, a hexanol, a heptanol, an octanol, a nonanol, a decanol, an undecanol, or mixtures thereof. In other embodiments, the alcohol compound can comprise, consist essentially of, or consist of, methanol, ethanol, 1-propanol, 2-propanol, 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, or mixtures thereof.

Additionally or alternatively, the catalyst system can be deactivated by contact with an aqueous solution (e.g., an aqueous Group 1 metal hydroxide solution or an aqueous mineral acid solution). Such deactivation processes to deactivate the catalyst system can also potentially remove a portion, or substantially all, of the metal catalyst system components from the oligomer product.

In the processes described herein, the processes can further comprise a step of separating unreacted monomer (e.g., 1-hexene) and/or the oligomer product from the catalyst system or deactivated catalyst system. Various suitable separations steps can be employed, as would be recognized by those of skill in the art. In an embodiment, and not limited thereto, a filtration step can be used.

Consistent with embodiments of this invention, a heavy oligomer product can be isolated. One such technique for isolating the heavy oligomer product can comprise a step of removing at least a portion of unreacted 1-hexene and light 1-hexene oligomers (at least a portion of $C_{12}$ to $C_{24}$, $C_{12}$ to $C_{30}$, or $C_{12}$ to $C_{36}$ oligomers) from the oligomer product. In these and other embodiments, various suitable separation or isolation steps can be employed, as would be recognized by those of skill in the art. In an embodiment, such separation or isolation steps can include one or more batch or continuous flash processes, one or more batch or continuous distillation processes, and combinations thereof. In another embodiment, a flash process at atmospheric or any suitable sub-atmospheric pressure can be utilized, while in yet another embodiment, a distillation process at atmospheric or any suitable sub-atmospheric pressure can be utilized. Suitable sub-atmospheric pressures can include, but are not limited to, less than 100 ton (13.3 kPa), less than 50 (6.67 kPa) ton, less than 10 ton (1.33 kPa), or less than 5 ton (0.67 kPa). The conditions that are used to isolate the heavy oligomer product can be varied based on the desired viscosity properties (e.g., viscosity index, pour point, viscosity at 40° C., viscosity at 100° C., etc.), and the identity and/or quantity of the particular oligomer to be removed to isolate the heavy oligomer product.

Consistent with embodiments of this invention, the heavy oligomer product can hydrogenated to form the hydrogenated oligomer composition. Any suitable hydrogenation process and associated catalyst can be used, and such hydrogenation processes and catalysts (e.g., platinum, rhenium, palladium, nickel, etc.) are well known to those of skill in the art. Generally, the heavy oligomer product can be hydrogenated to provide a hydrogenated oligomer composition having a desired degree of saturation (which can be quantified with a bromine number or bromine index). Embodiments of the present invention also are directed to and encompass any hydrogenated oligomer composition produced by any of the processes disclosed herein. Hence, the hydrogenated oligomer composition can have any of the characteristics or properties of any hydrogenated oligomer composition disclosed herein (e.g., viscosity index, pour point, viscosity at 40° C., viscosity at 100° C., etc.).

For instance, the hydrogenated oligomer composition can comprise at least 80 wt. % monomer units derived from 1-hexene, and can be characterized by a 100° C. kinematic viscosity in a range from 75 to 150 cSt, a viscosity index in a range from 150 to 180, and a pour point in a range from −20 to −40° C.; or the hydrogenated oligomer composition can comprise at least 95 wt. % monomer units derived from 1-hexene, and can be characterized by a 100° C. kinematic viscosity in a range from 80 to 125 cSt, a viscosity index in a range from 150 to 170, and a pour point in a range from −25 to −40° C.; or the hydrogenated oligomer composition can comprise at least 98 wt. % monomer units derived from 1-hexene, and can be characterized by a 100° C. kinematic viscosity in a range from 85 to 115 cSt, a viscosity index in a range from 155 to 165, and a pour point in a range from −25 to −35° C. Moreover, in one embodiment, the hydrogenated oligomer composition can contain less than 0.5 wt. % hydrogenated monomer, and less than 1 wt. % hydrogenated oligomers having 24 carbon atoms or less, 30 carbon atoms or less, or 36 carbon atoms or less. In another embodiment, the hydrogenated oligomer composition can contain less than 0.2 wt. % hydrogenated monomer, and less than 0.5 wt. % hydrogenated oligomers having 24 carbon atoms or less, 30 carbon atoms or less, or 36 carbon atoms or less.

Catalyst Systems

In the processes disclosed herein, an olefin feedstock comprising at least 80 wt. % 1-hexene can be contacted with a catalyst system comprising (i) a metallocene compound, (ii) a chemically-treated solid oxide, and (iii) optionally, an organoaluminum compound, thereby forming an oligomer product under oligomerization conditions. Any metallocene-based catalyst system suitable for the oligomerization of 1-hexene, and containing the aforementioned components, can be employed in this invention.

The metallocene compound can comprise, for example, a transition metal (one or more than one) from Groups 3-10 of the Periodic Table of the Elements. In one embodiment, the metallocene compound can comprise a Group 3, 4, 5, or 6 transition metal, or a combination of two or more transition metals. The metallocene compound can comprise chromium, titanium, zirconium, hafnium, vanadium, or a combination thereof, in some embodiments, or can comprise chromium, titanium, zirconium, hafnium, or a combination thereof, in other embodiments. Accordingly, the metallocene compound can comprise chromium, or titanium, or zirconium, or hafnium, either singly or in combination. In some embodiments, the metallocene compound can comprise zirconium. Moreover, catalyst systems comprising two or more metallocene compounds, wherein each metallocene compound independently can comprise chromium, titanium, zirconium, hafnium, vanadium, or a combination thereof, are contemplated and encompassed herein.

The metallocene compound can comprise a bridged metallocene compound. In one embodiment, the metallocene compound can comprise a bridged zirconium or hafnium based metallocene compound. In another embodiment, the metallocene compound can comprise a bridged zirconium or hafnium based metallocene compound with a carbon bridging atom or a silicon bridging atom. In yet another embodiment, the metallocene compound can comprise a bridged zirconium based metallocene with a cyclopentadienyl group and a carbon bridging atom or a silicon bridging atom. In still another embodiment, the metallocene compound can comprise a bridged zirconium based metallocene with two cyclopentadienyl groups and a carbon bridging atom or a silicon bridging atom.

In these and other embodiments, the bridged metallocene compound can contain an alkyl substituent (e.g., n-butyl, n-propyl) on the bridging atom(s). Additionally or alternatively, the bridged metallocene compound can contain an alkyl substituent, for example, on the bridging atom(s) and/or on a cyclopentadienyl group.

The metallocene compound is not limited solely to the bridged metallocene compounds such as described above. Other suitable bridged metallocene compounds are disclosed in U.S. Pat. Nos. 7,026,494, 7,041,617, 7,226,886, 7,312,283, 7,517,939, and 7,619,047.

In certain embodiments of this invention, the catalyst system can contain a metallocene compound, and the metallocene compound can comprise an unbridged metallocene compound. In one embodiment, the metallocene compound can comprise an unbridged zirconium or hafnium based metallocene compound and/or an unbridged zirconium and/or hafnium based dinuclear metallocene compound. In another embodiment, the metallocene compound can comprise an unbridged zirconium or hafnium based metallocene compound containing two cyclopentadienyl groups, two indenyl groups, or a cyclopentadienyl and an indenyl group. In another embodiment, the metallocene compound can comprise an unbridged zirconium or hafnium based metallocene compound containing two cyclopentadienyl groups. In another embodiment, the metallocene compound can comprise an unbridged zirconium based metallocene compound containing two cyclopentadienyl groups. In another embodiment, the metallocene compound can comprise an unbridged zirconium or hafnium based metallocene compound containing two indenyl groups. In another embodiment, the metallocene compound can comprise an unbridged zirconium or hafnium based metallocene compound containing a cyclopentadienyl and an indenyl group. In yet another embodiment, the metallocene compound can comprise an unbridged zirconium based metallocene compound containing a cyclopentadienyl and an indenyl group. In still another embodiment, the metallocene compound can comprise an unbridged zirconium based metallocene compound containing a cyclopentadienyl group and an indenyl group with an alkenyl substituent.

In these and other embodiments, the unbridged metallocene compound can contain an alkyl substituent (e.g., n-butyl, n-propyl) on one or both cyclopentadienyl-type groups (e.g., a cyclopentadienyl group, an indenyl group). Accordingly, the metallocene compound can contain an alkyl-substituted cyclopentadienyl group.

Illustrative and non-limiting examples of bridged and unbridged metallocene compounds that are suitable for use as metallocene compounds described herein can include the following compounds (ph=phenyl):

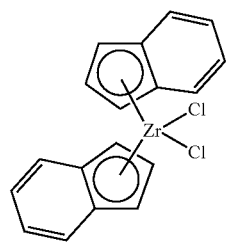

(1)

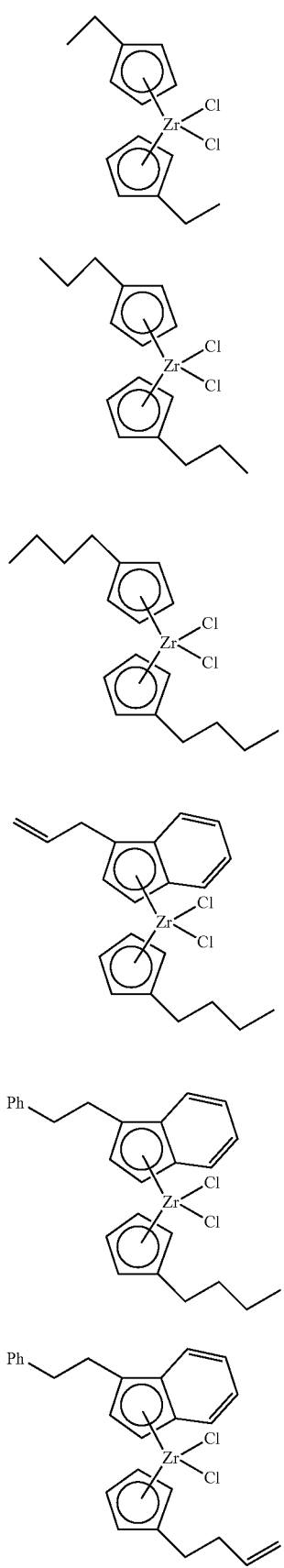
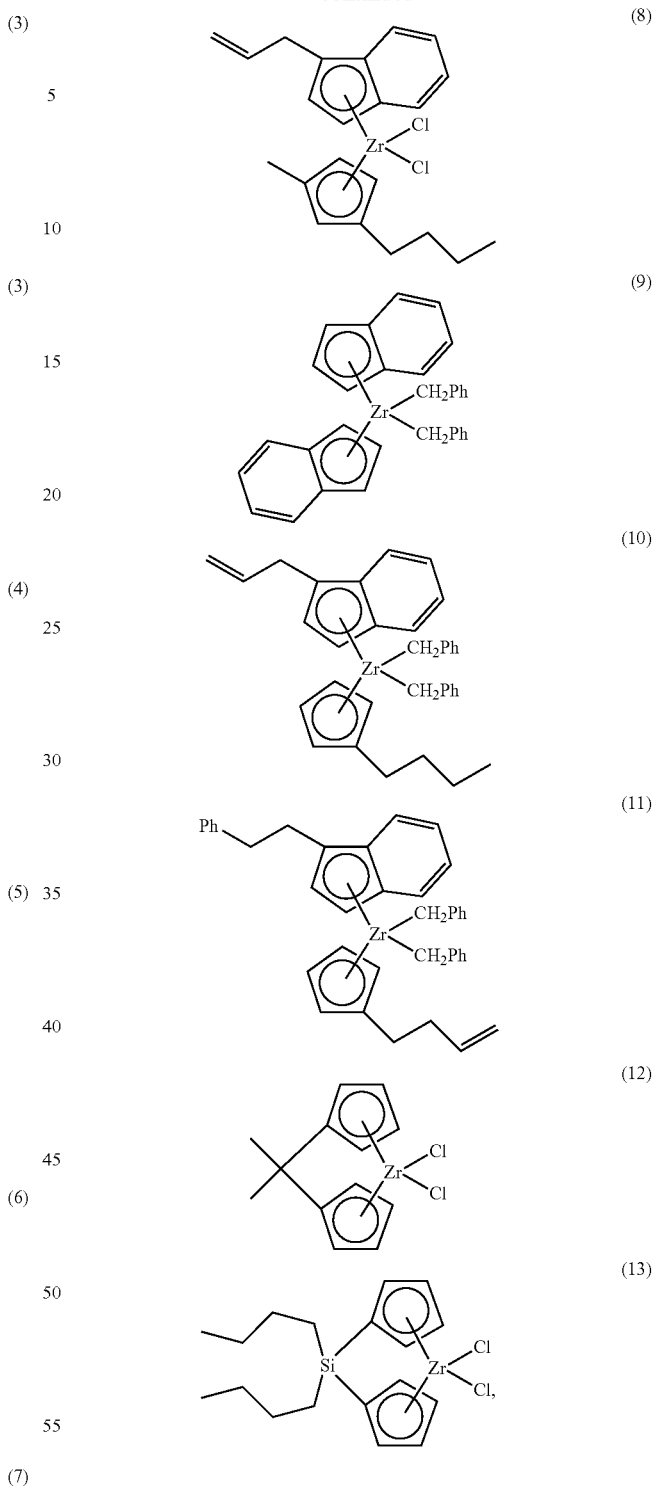

or any combination thereof.

The metallocene compound is not limited solely to bridged and unbridged metallocene compounds such as described above, or to suitable unbridged metallocene compounds disclosed in U.S. Pat. Nos. 7,199,073, 7,226,886, 7,312,283, and 7,619,047. For example, the metallocene compound can comprise an unbridged dinuclear metallocene compound, such as those described in U.S. Pat. Nos. 7,919,639 and 8,080,681. Illustrative and non-limiting examples of dinuclear metallocene compounds suitable for use in the present invention can include the following compounds:

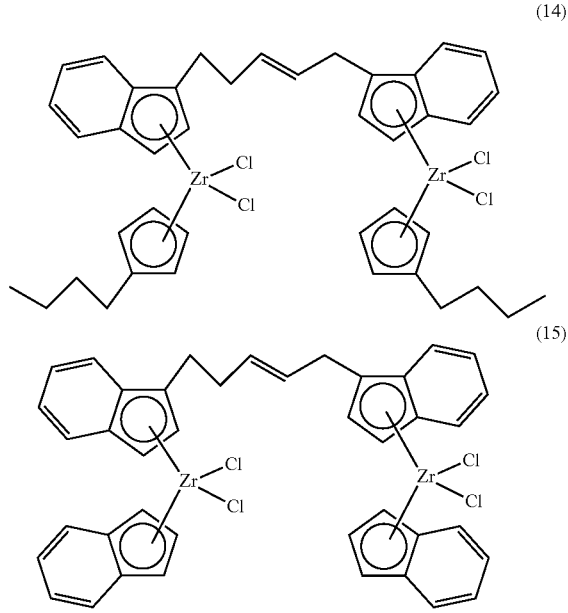

or any combination thereof.

The catalyst systems of the present invention, in addition to a metallocene compound (one or more), can contain a chemically-treated solid oxide and, optionally, an organoaluminum compound. In one embodiment, the chemically-treated solid oxide can comprise a solid oxide treated with an electron-withdrawing anion. Alternatively, in another embodiment, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294,599, 7,601,665, 7,884,163, 8,309,485, 8,623,973, 8,703,886, and 9,023,959.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-boria, aluminophosphate-silica, and titania-zirconia. The solid oxide used herein also can encompass oxide materials such as silica-coated alumina, as described in U.S. Pat. No. 7,884,163.

Accordingly, in one embodiment, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another embodiment, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, or any combination thereof. In another embodiment, the solid oxide can comprise silica, alumina, titania, zirconia, magnesia, boria, zinc oxide, any mixed oxide thereof, or any combination thereof. In yet another embodiment, the solid oxide can comprise silica-alumina, silica-coated alumina, silica-titania, silica-zirconia, alumina-boria, or any combination thereof. In still another embodiment, the solid oxide can comprise silica, alumina, silica-alumina, silica-coated alumina, or any mixture thereof; alternatively, silica; alternatively, alumina; alternatively, silica-alumina; or alternatively, silica-coated alumina.

The silica-alumina or silica-coated alumina solid oxide materials which can be used can have a silica content from 5 to 95% by weight. In one embodiment, the silica content of these solid oxides can be from 10 to 80%, or from 20% to 70%, silica by weight. In another embodiment, such materials can have silica contents ranging from 15% to 60%, or from 25% to 50%, silica by weight. The solid oxides contemplated herein can have any suitable surface area, pore volume, and particle size, as would be recognized by those of skill in the art.

The electron-withdrawing component used to treat the solid oxide can be any component that can increase the Lewis or Bronsted acidity of the solid oxide upon treatment (as compared to the solid oxide that is not treated with at least one electron-withdrawing component). According to one embodiment, the electron-withdrawing component can be an electron-withdrawing anion derived from a salt, an acid, or other compound, such as a volatile organic compound, that can serve as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, and molybdate, including mixtures and combinations thereof. In addition, other ionic or non-ionic compounds that can serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some embodiments provided herein. In other embodiments, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof. Yet, in other embodiments, the electron-withdrawing anion can comprise fluoride and/or sulfate.

The chemically-treated solid oxide generally can contain from 1 to 25 wt. % of the electron-withdrawing anion, based on the weight of the chemically-treated solid oxide. In particular embodiments provided herein, the chemically-treated solid oxide can contain from 1 to 20 wt. %, from 2 to 20 wt. %, from 3 to 20 wt. %, from 2 to 15 wt. %, from 3 to 15 wt. %, from 3 to 12 wt. %, or from 4 to 10 wt. %, of the electron-withdrawing anion, based on the total weight of the chemically-treated solid oxide.

In an embodiment, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, or any combination thereof. In another embodiment, the chemically-treated solid oxide employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, or any combination thereof. In yet another embodiment, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the chemically-treated solid oxide can comprise a fluorided solid oxide, while in other embodiments, the chemically-treated solid oxide can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485. Other suitable processes and procedures for preparing chemically-treated solid oxides (e.g., fluorided solid oxides, sulfated solid oxides, etc.) are well known to those of skill in the art.

In certain embodiments of this invention, the catalyst system can further comprise an organoaluminum compound. In an embodiment, the organoaluminum compound can comprise, can consist essentially of, or can be, a trialkylaluminum compound. Specific non-limiting examples of suitable compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, and diethylaluminum chloride, or combinations thereof. In one embodiment, the organoaluminum can comprise, consist essentially of, or can be a trialkylaluminum compound, and the trialkylaluminum compound can comprise, can consist essentially of, or can be, trimethylaluminum, triethylaluminum, triisobutylaluminum, or any combination thereof, while in another embodiment, the organoaluminum compound can comprise, can comprise, consist essentially of, or can be, a trialkylaluminum compound, and the trialkylaluminum compound can comprise, can consist essentially of, or can be, trimethylaluminum; alternatively, triethylaluminum (TEA); or alternatively, triisobutylaluminum (TIBA).

While not a requirement, the catalyst system can further comprise an aluminoxane compound, an organoboron or organoborate compound, an ionizing ionic compound, an organozinc compound, an organomagnesium compound, or an organolithium compound, and this includes any combinations of these materials. Accordingly, the catalyst system can further contain, in certain embodiments of this invention, an aluminoxane compound; alternatively, an organoboron or organoborate compound; alternatively, an ionizing ionic compound; alternatively, an organozinc compound; alternatively, an organomagnesium compound; or alternatively, an organolithium compound.

Representative and non-limiting examples of aluminoxanes include methylaluminoxane, a modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentyl-aluminoxane, 2-pentylaluminoxane, 3-pentylaluminoxane, iso-pentylaluminoxane, and neopentylaluminoxane, or any combination thereof. Representative and non-limiting examples of organoboron/organoborate compounds include N,N-dimethylanilinium tetrakis(pentafluorophenyl)-borate, triphenylcarbenium tetrakis(pentafluorophenyl)borate, lithium tetrakis-(pentafluorophenyl)borate, N,N-dimethylanilinium tetrakis [3,5-bis(trifluoromethyl)phenyl]borate, triphenylcarbenium tetrakis[3,5-bis(trifluoromethyl)phenyl]borate, tris(pentafluorophenyl)boron, and tris [3,5-bis(trifluoromethyl)phenyl]boron, or mixtures thereof.

Examples of ionizing ionic compounds can include, but are not limited to, the following compounds: tri(n-butyl)ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis [3,5-bis(trifluoro-methyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis [3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis [3,5-bis(trifluoromethyl)phenyl]borate, triphenylcarbenium tetrakis (pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis [3,5-bis(trifluoromethyl)phenyl]borate, tropylium tetrakis (pentafluorophenyl) borate, lithium tetrakis (pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis (m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis (pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis (pentafluorophenyl)aluminate, sodium tetraphenylaluminate, sodium tetrakis(p-tolyl)-aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis (3,5-dimethylphenyl)aluminate, and potassium tetrafluoroaluminate, or combinations thereof.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, and di(trimethylsilylmethyl)zinc, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, and trimethylsilylmethylmagnesium phenoxide, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl)methyllithium, and allyllithium, or combinations thereof.

Organoaluminum compounds and other co-catalysts that can be used in the catalyst systems of this invention are not limited to those materials described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485.

In accordance with embodiments of this invention, a catalyst system is provided which comprises a metallocene compound, a chemically-treated solid oxide, and an organoaluminum compound. In some embodiments, this catalyst composition can be substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these embodiments, the catalyst system can have catalyst activity, discussed herein, in the substantial absence of aluminoxanes, organoboron or organoborate compounds, ionizing ionic compounds, and/or other similar materials. For example, a catalyst system of the present invention can consist essentially of a metallocene compound, a chemically-treated solid oxide, and an organoaluminum compound, wherein no other materials are present in the catalyst system which would increase/decrease the activity of the catalyst system by more than 10% from the catalyst activity of the catalyst system in the absence of said materials.

This invention further encompasses methods of making these catalyst systems, such as, for example, contacting the respective catalyst components in any order or sequence. In one embodiment, the catalyst system can be produced by a process comprising contacting the metallocene compound and the chemically-treated solid oxide, while in another embodiment, the catalyst system can be produced by a process comprising contacting, in any order, the metallocene compound, the chemically-treated solid oxide, and the organoaluminum co-catalyst (e.g., TEA or TIBA).

While not being limited thereto, the weight ratio of the chemically-treated solid oxide to the metallocene compound often can fall within a range from 20:1 to 1500:1. For instance, the weight ratio of the chemically-treated solid oxide to the metallocene compound can be at least 20:1, 50:1, 60:1, or 70:1; alternatively, or additionally, the maximum weight ratio of the chemically-treated solid oxide to the metallocene compound can be 1500:1, 1000:1, 800:1, 600:1, or 500:1. Generally, the weight ratio of the chemically-treated solid oxide to the metallocene compound can be in a range from any minimum weight ratio disclosed herein to any maximum weight ratio disclosed herein. Therefore, suitable non-limiting ranges for the weight ratio of the chemically-treated solid oxide to the metallocene compound can include the following ranges: from 20:1 to 1500:1, from 20:1 to 1000:1, from 20:1 to 500:1, from 50:1 to 1500:1, from 50:1 to 1000:1, from 50:1 to 800:1, from 60:1 to 800:1, from 60:1 to 600:1, from 70:1 to 1000:1, from 70:1 to 600:1, or from 70:1 to 500:1. Other appropriate ranges for the weight ratio of the chemically-treated solid oxide to the metallocene compound are readily apparent from this disclosure. If more than one metallocene compound and/or more than chemically-treated solid oxide is/are employed, this ratio is based on the total weights of the respective components.

The molar ratio of the organoaluminum compound (based on moles of aluminum) to the metallocene compound (based on the moles of transition metal) often ranges from 5:1 to 5000:1. For instance, the molar ratio of aluminum to transition metal can be at least 5:1, 10:1, 15:1 or 50:1; alternatively, or additionally, the maximum molar ratio aluminum to transition metal can be 5000:1, 2500:1, 1000:1, 250:1, or 150:1. Generally, the molar ratio of aluminum of the organoaluminum compound to transition metal of the metallocene compound can be in a range from any minimum molar ratio disclosed herein to any maximum molar ratio disclosed herein. Therefore, suitable non-limiting ranges for the molar ratio can include the following ranges: from 5:1 to 5000:1, from 5:1 to 1000:1, from 5:1 to 250:1, from 10:1 to 2500:1, from 10:1 to 1000:1, from 10:1 to 150:1, from 15:1 to 150:1, or from 50:1 to 1000:1. Other appropriate ranges for the molar ratio of aluminum of the organoaluminum compound to transition metal of the metallocene compound are readily apparent from this disclosure. If more than one metallocene compound and/or more than organoaluminum co-catalyst is/are employed, this ratio is based on the total moles of the respective components.

In accordance with the present invention, a process is provided that comprises contacting an olefin feedstock comprising (or consisting essentially of, or consisting of) 1-hexene with a catalyst system comprising (or consisting essentially of, or consisting of) (i) a metallocene compound, (ii) a chemically-treated solid oxide, and (iii) an optional organoaluminum co-catalyst, thereby forming an oligomer product under oligomerization conditions. While not being limited thereto, the molar ratio of 1-hexene to the metallocene compound often ranges from $1\times10^3:1$ to $1\times10^9:1$. For instance, the molar ratio of 1-hexene to the metallocene compound can be at least $1\times10^3:1$, $5\times10^3:1$, $1\times10^4:1$, $5\times10^4:1$, or $1\times10^5:1$; alternatively, or additionally, the maximum molar ratio of 1-hexene to the metallocene compound can be $1\times10^9:1$, $5\times10^8:1$, $1\times10^8:1$, $5\times10^7:1$, $1\times10^7:1$, $5\times10^6:1$, or $1\times10^6:1$. Generally, the molar ratio of 1-hexene to the metallocene compound can be in a range from any minimum molar ratio disclosed herein to any maximum molar ratio disclosed herein. Therefore, suitable non-limiting ranges for the molar ratio of 1-hexene to the metallocene compound can include the following ranges: from $1\times10^3:1$ to $1\times10^9:1$, from $5\times10^3:1$ to $1\times10^9:1$, from $5\times10^3:1$ to $5\times10^8:1$, from $1\times10^4:1$ to $1\times10^8:1$, from $5\times10^4:1$ to $1\times10^8:1$, from $5\times10^4:1$ to $5\times10^7:1$, from $1\times10^5:1$ to $5\times10^7:1$, from $1\times10^5:1$ to $1\times10^7:1$, from $1\times10^5:1$ to $5\times10^6:1$, or from $1\times10^5:1$ to $1\times10^6:1$. Other appropriate ranges for the molar ratio of 1-hexene to the metallocene compound are readily apparent from this disclosure.

Unexpectedly, catalyst systems of the present invention can have a high activity. Typically, the catalyst systems have an activity of at least 25,000, at least 30,000, at least 35,000, or at least 40,000 grams of oligomer product per gram of metallocene compound per hour (g/g/hr), and often can range up to 75,000-100,000 g/g/hr. In another embodiment, the activity of the catalyst system can be at least 100, at least 400, at least 800, at least 1,000, at least 1,500, at least 2,000, at least 3,000, at least 4,000, at least 5,000, or at least 6,000 grams of oligomer product per gram of organoaluminum co-catalyst (when used) per hour, and often can range up to 10,000-15,000 g/g/hr. Generally, the activity of the catalyst system can be measured using reaction conditions of 45 or 65° C., a molar ratio of 1-hexene to the metallocene compound of $1.5\times10^6:1$, an organoaluminum compound to metallocene compound molar ratio of 400:1, and at ambient pressure.

Lubricant Compositions

This invention also contemplates and encompasses any compositions (e.g., lubricant compositions or lubricant formulations) or base oil compositions that comprise the hydrogenated oligomer compositions disclosed herein.

In one particular embodiment of this invention, the base oil composition (or the lubricant composition) can have a nominal 100° C. kinematic viscosity ranging from 30 to 50 cSt. In this embodiment, the base oil composition (or the lubricant composition) can comprise (i) any of the hydrogenated oligomer compositions disclosed herein, and (ii) a low viscosity PAO having a 100° C. kinematic viscosity in a range from 1 to 20 cSt. The weight ratio of the hydrogenated oligomer composition:low viscosity PAO can be in a range from 25:75 to 90:10, and the base oil composition (or the lubricant composition) can have a 100° C. kinematic viscosity in the range from 30 to 50 cSt.

The base oil composition (or the lubricant composition) product can have a 100° C. kinematic viscosity ranging from 30 to 50 cSt. For instance, the base oil composition (or the lubricant composition) can have a minimum 100° C. kinematic viscosity of 30, 32, 35, or 37 cSt; alternatively, or additionally, the maximum 100° C. kinematic viscosity of the base oil composition (or the lubricant composition) can be 50, 47, 45, or 43 cSt. Generally, the 100° C. kinematic viscosity of the base oil composition (or the lubricant composition) can be in a range from any minimum kinematic viscosity disclosed herein to any maximum kinematic viscosity disclosed herein. Therefore, suitable non-limiting ranges for the 100° C. kinematic viscosity of the base oil composition (or the lubricant composition) can include the following ranges: from 30 to 50 cSt, from 30 to 47 cSt, from 30 to 45 cSt, from 30 to 43 cSt, from 32 to 47 cSt, from 32 to 43 cSt, from 35 to 50 cSt, from 35 to 47 cSt, from 35 to 45 cSt, from 37 to 50 cSt, from 37 to 47 cSt, from 37 to 45 cSt, or from 37 to 43 cSt. Other appropriate ranges for the 100° C. kinematic viscosity of the base oil composition (or the lubricant composition) are readily apparent from this disclosure. Generally, the viscosities of the base oil composition (or the lubricant composition) can be measured using ASTM D7042-04 or ASTM D445-06.

Consistent with embodiments of this invention, the base oil composition (or the lubricant composition) having a nominal 100° C. kinematic viscosity in any range from 30 to 50 cSt disclosed herein can have a 40° C. kinematic viscosity ranging from 300 to 500 cSt. For instance, the base oil composition (or the lubricant composition) can have a minimum 40° C. kinematic viscosity of 300, 325, 350, or 375 cSt; alternatively, or additionally, the maximum 40° C. kinematic viscosity of the base oil composition (or the lubricant composition) can be 500, 475, 450, or 425 cSt. Generally, the 40° C. kinematic viscosity of the base oil composition (or the lubricant composition) can be in a range from any minimum 40° C. kinematic viscosity disclosed herein to any maximum 40° C. kinematic viscosity disclosed herein. Therefore, suitable non-limiting ranges for the 40° C. kinematic viscosity of the base oil composition (or the lubricant composition) can include the following ranges: from 300 to 500 cSt, from 300 to 450 cSt, from 325 to 475 cSt, from 325 to 425 cSt, from 350 to 500 cSt, from 350 to 450 cSt, from 350 to 425 cSt, from 375 to 500 cSt, from 375 to 475 cSt, from 375 to 450 cSt, or from 375 to 425 cSt. Other appropriate ranges for the 40° C. kinematic viscosity of the base oil composition (or the lubricant composition) are readily apparent from this disclosure.

The base oil composition (or the lubricant composition) having a nominal 100° C. kinematic viscosity in any range from 30 to 50 cSt disclosed herein can have a viscosity index of from 130 to 180. For instance, the minimum viscosity index of the base oil composition (or the lubricant composition) can be at least 130, 135, 140, or 145; alternatively, or additionally, the maximum viscosity index can be 180, 170, 165, or 160. Generally, the viscosity index of the base oil composition (or the lubricant composition) can be in a range from any minimum viscosity index disclosed herein to any maximum viscosity index disclosed herein. Therefore, suitable non-limiting ranges for the viscosity index of the base oil composition (or the lubricant composition) can include the following ranges: from 130 to 180, from 130 to 165, from 130 to 160, from 135 to 170, from 130 to 165, from 140 to 180, from 140 to 170, from 140 to 165, from 145 to 170, or from 145 to 160. Other appropriate ranges for the viscosity index of the base oil composition (or the lubricant composition) are readily apparent from this disclosure. Generally, the viscosity index of the base oil composition (or the lubricant composition) can be measured using ASTM D7042-04.

The pour point of the base oil composition (or the lubricant composition) having a nominal 100° C. kinematic viscosity in any range from 30 to 50 cSt disclosed herein typically can be less than or equal to −25° C. For instance, the minimum pour point of the base oil composition (or the lubricant composition) can be −60, −55, −50, or −48° C.;

alternatively, or additionally, the maximum pour point can be −25, −30, or −32° C. Generally, the pour point of the base oil composition (or the lubricant composition) can be in a range from any minimum pour point temperature disclosed herein to any maximum pour point temperature disclosed herein. Therefore, suitable non-limiting ranges for the pour point of the base oil composition (or the lubricant composition) can include the following ranges: less than −25° C., less than −30° C., less than −32° C., from −25 to −60° C., from −25 to −55° C., from −25 to −50° C., from −25 to −48° C., from −30 to −60° C., from −30 to −55° C., from −30 to −50° C., from −32 to −55° C., or from −32 to −48° C. Other appropriate ranges for the pour point of the base oil composition (or the lubricant composition) are readily apparent from this disclosure. Generally, the pour point of the base oil composition (or the lubricant composition) can be measured using ASTM D97-04.

While not being limited thereto, the weight ratio of the hydrogenated oligomer composition:low viscosity PAO in the base oil composition (or the lubricant composition) having a nominal 100° C. kinematic viscosity in any range from 30 to 50 cSt disclosed herein can often fall within a range from 25:75 to 90:10. In one embodiment, the weight ratio of the hydrogenated oligomer composition:low viscosity PAO can be in a range from 30:70 to 85:15, or from 35:65 to 80:20, while in another embodiment, the weight ratio can be in a range from 30:70 to 75:25, or from 35:65 to 75:25, and in yet another embodiment, from 40:60 to 75:25, from 50:50 to 75:25, or from 60:40 to 75:25. Other appropriate ranges for the weight ratio of the hydrogenated oligomer composition:low viscosity PAO in the base oil composition (or the lubricant composition) are readily apparent from this disclosure.

The hydrogenated oligomer composition in the base oil composition (or the lubricant composition) having a nominal 100° C. kinematic viscosity in any range from 30 to 50 cSt disclosed herein can be any hydrogenated oligomer composition disclosed herein, and have any properties or characteristics of the hydrogenated oligomer composition disclosed herein. As an example, the hydrogenated oligomer composition can comprise at least 80 wt. % monomer units derived from 1-hexene, and can be characterized by a 100° C. kinematic viscosity in a range from 75 to 150 cSt, a viscosity index in a range from 150 to 180, and a pour point in a range from −20 to −40° C. As another example, the hydrogenated oligomer composition can comprise at least 95 wt. % monomer units derived from 1-hexene, and can be characterized by a 100° C. kinematic viscosity in a range from 80 to 125 cSt, a viscosity index in a range from 150 to 170, and a pour point in a range from −25 to −40° C. And, in yet another example, the hydrogenated oligomer composition can comprise at least 98 wt. % monomer units derived from 1-hexene, and can be characterized by a 100° C. kinematic viscosity in a range from 85 to 115 cSt, a viscosity index in a range from 155 to 165, and a pour point in a range from −25 to −35° C. Other combinations of the wt. % monomer units derived from 1-hexene, 100° C. kinematic viscosity, viscosity index, and pour point either alone or in addition with other properties such as the amount of hydrogenated oligomer having less than a specified wt. % of hydrogenated oligomer, having less than a specified number of carbon atoms, and/or the presence or absence of a discernable crystallization above −40° C. for the hydrogenated oligomer composition in the base oil composition (or the lubricant composition) having a nominal 100° C. kinematic viscosity in any range from 30 to 50 cSt are readily apparent from this disclosure. These features for the hydrogenated oligomer composition in the base oil composition (or the lubricant composition) having a nominal 100° C. kinematic viscosity in any range from 30 to 50 cSt are independently described herein and may be utilized in any combination and without limitation to further describe the hydrogenated oligomer composition in the base oil composition (or the lubricant composition) having a nominal 100° C. kinematic viscosity in any range from 30 to 50 cSt.

Referring now to the low viscosity PAO, the low viscosity PAO in the base oil composition (or the lubricant composition) can be described as having a specified 100° C. kinematic viscosity, a specified viscosity index, a specified pour point, comprise monomer units derived from specified monomer(s), have specified wt. % of monomer units derived from specified monomer(s), and/or be substantially free of monomer units derived from a specified monomer(s). These features of the low viscosity PAO used in the base oil composition (or lubricant composition) are independently described herein. These independent features can be utilized in any combination, and without limitation to further describe the low viscosity PAO in the base oil composition described herein, and can further be utilized in any combination, and without limitation, with the independently described hydrogenated oligomer composition to describe the base oil composition (or the lubricant composition) having a nominal 100° C. kinematic viscosity in any range from 30 to 50 cSt. Generally, the low viscosity PAO—in the base oil composition (or the lubricant composition) that can have a nominal 100° C. kinematic viscosity in any range from 30 to 50 cSt disclosed herein—can have a 100° C. kinematic viscosity in a range from 1 to 20 cSt. For instance, the low viscosity PAO can have a minimum 100° C. kinematic viscosity of 1, 2, or 5 cSt; alternatively, or additionally, the maximum 100° C. kinematic viscosity of the low viscosity PAO can be 20, 15, 12, or 10 cSt. Generally, the 100° C. kinematic viscosity of the low viscosity PAO can be in a range from any minimum 100° C. kinematic viscosity disclosed herein to any maximum 100° C. kinematic viscosity disclosed herein. Therefore, suitable non-limiting ranges for the 100° C. kinematic viscosity of the low viscosity PAO can include the following ranges: from 1 to 20 cSt, from 1 to 15 cSt, from 1 to 12 cSt, from 1 to 10 cSt, from 2 to 20 cSt, from 2 to 15 cSt, from 2 to 12 cSt, from 2 to 10 cSt, from 5 to 20 cSt, from 5 to 15 cSt, from 5 to 12 cSt, or from 5 to 10 cSt. Other appropriate ranges for the 100° C. kinematic viscosity of the low viscosity PAO are readily apparent from this disclosure. As non-limiting examples, the 100° C. kinematic viscosity of the low viscosity PAO can fall within a range from 2.3 cSt to 2.7 cSt; alternatively, from 2.6 cSt to 3.4 cSt; alternatively, from 3.6 cSt to 4.4 cSt; alternatively, from 4.6 cSt to 5.4 cSt; alternatively, from 5.6 cSt to 6.4 cSt; alternatively, from 6.6 cSt to 7.4 cSt; alternatively, from 7.6 cSt to 8.4 cSt; alternatively, from 8.6 cSt to 9.4 cSt; or alternatively, from 9.6 cSt to 10.4 cSt.

The low viscosity PAO in the base oil composition (or the lubricant composition) having a nominal 100° C. kinematic viscosity in any range from 30 to 50 cSt disclosed herein can have a viscosity index of from 90 to 200. For instance, the minimum viscosity index of the low viscosity PAO can be at least 90, 95, 100, 110 or 120; alternatively, or additionally, the maximum viscosity index can be 200, 180, 160, or 155. Generally, the viscosity index of the low viscosity PAO can be in a range from any minimum viscosity index disclosed herein to any maximum viscosity index disclosed herein. Therefore, suitable non-limiting ranges for the viscosity index of the low viscosity PAO can include the following ranges: from 90 to 200, from 90 to 160, from 95 to 200, from 95 to 180, from 95 to 160, from 100 to 200, from 100 to 160, from 110 to 180, from 110 to 160, from 120 to 200, from 120 to 180, or from 120 to 155. Other appropriate ranges for the viscosity index of the low viscosity PAO are readily apparent from this disclosure.

The pour point of the low viscosity PAO in the base oil composition (or the lubricant composition) having a nominal 100° C. kinematic viscosity in any range from 30 to 50 cSt disclosed herein typically can be less than or equal to −20° C. For instance, the minimum pour point of the low viscosity PAO can be −85, −80, −75, or −60° C.; alternatively, or additionally, the maximum pour point can be −20, −23, −26, −29, or −32° C. Generally, the pour point of the low viscosity PAO can be in a range from any minimum pour point temperature disclosed herein to any maximum pour point temperature disclosed herein. Therefore, suitable non-limiting ranges for the pour point of the low viscosity PAO can include the following ranges: less than −20° C., less than −26° C., less than −32° C., from −20 to −85° C., from −20 to −75° C., from −20 to −60° C., from −23 to −80° C., from −23 to −75° C., from −26 to −75° C., from −26 to −60° C., from −29 to −75° C., from −29 to −60° C., from −32 to −80° C., from −32 to −75° C., or from −32 to −60° C. Other appropriate ranges for the pour point of the low viscosity PAO are readily apparent from this disclosure.

Generally, the low viscosity PAO in the base oil composition (or the lubricant composition) having a nominal 100° C. kinematic viscosity in any range from 30 to 50 cSt disclosed herein can comprise monomer units derived from a $C_6$ to $C_{18}$ normal alpha olefin; alternatively, a $C_8$ to $C_{16}$ normal alpha olefin; or alternatively, 1-octene, 1-decene, 1-dodecene, 1-tetradecene, or any combination thereof. In an embodiment, the low viscosity PAO can comprise monomer units derived from 1-octene, 1-decene, 1-dodecene, or any combination thereof. In another embodiment, the viscosity PAO can comprise monomer units derived from 1-decene, 1-dodecene, 1-tetradecene, or any combination thereof. In yet another embodiment, the low viscosity PAO can comprise comprises monomer units derived from 1-decene, 1-dodecene, or a combination thereof. In still another embodiment, the low viscosity PAO can comprise monomer units derived from 1-octene; alternatively, 1-decene; alternatively, 1-dodecene; or alternatively, 1-tetradecene.

Consistent with certain embodiments of this invention, and beneficially, the low viscosity PAO used in the base oil composition (or the lubricant composition) having a nominal 100° C. kinematic viscosity in any range from 30 to 50 cSt disclosed herein can be substantially free of a 1-decene PAO, or substantially free of a predominantly 1-decene PAO. In an embodiment, the low viscosity PAO can contain less than 15 wt. %, less than 10 wt. %, less than 5 wt. %, or less than 1 wt. % of a PAO having at least 80 wt. %, at least 85 wt. %, at least 90 wt. %, at least 92.5 wt. %, at least 95 wt. %, or at least 97.5 wt. % monomer units derived from 1-decene. As an example, the low viscosity PAO can contain less than 15 wt. % of a PAO having at least 80 wt. % monomer units derived from 1-decene. As another example, the low viscosity PAO can contain less than 5 wt. % of a PAO having at least 90 wt. % monomer units derived from 1-decene. As yet another example, the low viscosity PAO can contain less than 1 wt. % of a PAO having at least 95 wt. % monomer units derived from 1-decene.

Also consistent with certain embodiments of this invention, and beneficially, the base oil composition (or the lubricant composition) having a nominal 100° C. kinematic viscosity in any range from 30 to 50 cSt disclosed herein can be substantially free of a 1-decene PAO, or substantially free of a predominantly 1-decene PAO. In an embodiment, the base oil composition (or the lubricant composition) can contain less than 10 wt. %, less than 5 wt. %, less than 2 wt. %, or less than 1 wt. % of a PAO having at least 80 wt. %, at least 85 wt. %, at least 90 wt. %, at least 92.5 wt. %, at least 95 wt. %, or at least 97.5 wt. % monomer units derived from 1-decene. As an example, the base oil composition (or the lubricant composition) can contain less than 10 wt. % of a PAO having at least 80 wt. % monomer units derived from 1-decene. As another example, the base oil composition (or the lubricant composition) can contain less than 5 wt. % of a PAO having at least 90 wt. % monomer units derived from 1-decene. As yet another example, the base oil composition (or the lubricant composition) can contain less than 1 wt. % of a PAO having at least 95 wt. % monomer units derived from 1-decene.

In one particular embodiment of this invention, the base oil composition (or the lubricant composition) can have a nominal 100° C. kinematic viscosity ranging from 80 to 120 cSt. In this embodiment, the base oil composition (or the lubricant composition) can comprise (i) any of the hydrogenated oligomer composition disclosed herein, and (ii) a high viscosity PAO having a 100° C. kinematic viscosity in a range from 75 to 150 cSt. The weight ratio of the hydrogenated oligomer composition:high viscosity PAO can be in a range from 25:75 to 80:20, and the base oil composition (or the lubricant composition) can have a 100° C. kinematic viscosity in the range from 80 to 120 cSt.

The base oil composition (or the lubricant composition) product can have a 100° C. kinematic viscosity ranging from 80 to 120 cSt. For instance, the base oil composition (or the lubricant composition) can have a minimum 100° C. kinematic viscosity of 80, 85, 90, or 95 cSt; alternatively, or additionally, the maximum 100° C. kinematic viscosity of the base oil composition (or the lubricant composition) can be 120, 115, 110, or 105 cSt. Generally, the 100° C. kinematic viscosity of the base oil composition (or the lubricant composition) can be in a range from any minimum kinematic viscosity disclosed herein to any maximum kinematic viscosity disclosed herein. Therefore, suitable non-limiting ranges for the 100° C. kinematic viscosity of the base oil composition (or the lubricant composition) can include the following ranges: from 80 to 120 cSt, from 80 to 115 cSt, from 80 to 105 cSt, from 85 to 120 cSt, from 85 to 115 cSt, from 85 to 105 cSt, from 90 to 120 cSt, from 90 to 110 cSt, from 90 to 105 cSt, from 95 to 120 cSt, from 95 to 115 cSt, from 95 to 110 cSt, or from 95 to 105 cSt. Other appropriate ranges for the 100° C. kinematic viscosity of the base oil composition (or the lubricant composition) are readily apparent from this disclosure.

Consistent with embodiments of this invention, the base oil composition (or the lubricant composition) having a nominal 100° C. kinematic viscosity in any range from 80 to 120 cSt disclosed herein can have a 40° C. kinematic viscosity ranging from 800 to 1800 cSt. For instance, the base oil composition (or the lubricant composition) can have a minimum 40° C. kinematic viscosity of 800, 900, 1000, or 1100 cSt; alternatively, or additionally, the maximum 40° C. kinematic viscosity of the base oil composition (or the lubricant composition) can be 1800, 1500, 1400, or 1300 cSt. Generally, the 40° C. kinematic viscosity of the base oil composition (or the lubricant composition) can be in a range from any minimum 40° C. kinematic viscosity disclosed herein to any maximum 40° C. kinematic viscosity disclosed herein. Therefore, suitable non-limiting ranges for the 40° C. kinematic viscosity of the base oil composition (or the lubricant composition) can include the following ranges: from 800 to 1800 cSt, from 800 to 1400 cSt, from 900 to 1500 cSt, from 900 to 1300 cSt, from 1000 to 1800 cSt, from 1000 to 1400 cSt, from 1000 to 1300 cSt, from 1100 to 1800 cSt, from 1100 to 1500 cSt, from 1100 to 1400 cSt, or from 1100 to 1300 cSt. Other appropriate ranges for the 40° C. kinematic viscosity of the base oil composition (or the lubricant composition) are readily apparent from this disclosure.

The base oil composition (or the lubricant composition) having a nominal 100° C. kinematic viscosity in any range from 80 to 120 cSt disclosed herein can have a viscosity index of from 160 to 200. For instance, the minimum viscosity index of the base oil composition (or the lubricant composition) can be at least 160, 165, or 170; alternatively, or additionally, the maximum viscosity index can be 200, 190, or 180. Generally, the viscosity index of the base oil composition (or the lubricant composition) can be in a range from any minimum viscosity index disclosed herein to any maximum viscosity index disclosed herein. Therefore, suitable non-limiting ranges for the viscosity index of the base oil composition (or the lubricant composition) can include the following ranges: from 160 to 200, from 160 to 190, from 160 to 180, from 165 to 200, from 165 to 190, from 165 to 180, from 170 to 200, from 170 to 190, or from 170 to 180. Other appropriate ranges for the viscosity index of the base oil composition (or the lubricant composition) are readily apparent from this disclosure.

The pour point of the base oil composition (or the lubricant composition) having a nominal 100° C. kinematic viscosity in any range from 80 to 120 cSt disclosed herein typically can be less than or equal to −25° C. For instance, the minimum pour point of the base oil composition (or the lubricant composition) can be −50, −45, or −38° C.; alternatively, or additionally, the maximum pour point can be −25, −28, or −30° C. Generally, the pour point of the base oil composition (or the lubricant composition) can be in a range from any minimum pour point temperature disclosed herein to any maximum pour point temperature disclosed herein. Therefore, suitable non-limiting ranges for the pour point of the base oil composition (or the lubricant composition) can include the following ranges: less than −25° C., less than −28° C., less than −30° C., from −25 to −50° C., from −25 to −45° C., from −25 to −38° C., from −28 to −50° C., from −28 to −38° C., from −30 to −50° C., from −30 to −45° C., or from −30 to −38° C. Other appropriate ranges for the pour point of the base oil composition (or the lubricant composition) are readily apparent from this disclosure.

While not being limited thereto, the weight ratio of the hydrogenated oligomer composition:high viscosity PAO in the base oil composition (or the lubricant composition) having a nominal 100° C. kinematic viscosity in any range from 80 to 120 cSt disclosed herein can often fall within a range from 25:75 to 80:20. In one embodiment, the weight ratio of the hydrogenated oligomer composition:high viscosity PAO can be in a range from 30:70 to 80:20, or from 35:65 to 80:20, while in another embodiment, the weight ratio can be in a range from 30:70 to 75:25, or from 35:65 to 65:35, and in yet another embodiment, from 40:60 to 75:25, from 40:60 to 60:40, or from 45:55 to 55:45. Other appropriate ranges for the weight ratio of the hydrogenated oligomer composition:high viscosity PAO in the base oil composition (or the lubricant composition) are readily apparent from this disclosure.

The hydrogenated oligomer composition in the base oil composition (or the lubricant composition) having a nominal 100° C. kinematic viscosity in any range from 80 to 120 cSt disclosed herein can be any hydrogenated oligomer composition disclosed herein, and have any properties or characteristics of the hydrogenated oligomer composition disclosed herein. As an example, the hydrogenated oligomer composition can comprise at least 80 wt. % monomer units derived from 1-hexene, and can be characterized by a 100° C. kinematic viscosity in a range from 75 to 150 cSt, a viscosity index in a range from 150 to 180, and a pour point in a range from −20 to −40° C. As another example, the hydrogenated oligomer composition can comprise at least 95 wt. % monomer units derived from 1-hexene, and can be characterized by a 100° C. kinematic viscosity in a range from 80 to 125 cSt, a viscosity index in a range from 150 to 170, and a pour point in a range from −25 to −40° C. And, in yet another example, the hydrogenated oligomer composition can comprise at least 98 wt. % monomer units derived from 1-hexene, and can be characterized by a 100° C. kinematic viscosity in a range from 85 to 115 cSt, a viscosity index in a range from 155 to 165, and a pour point in a range from −25 to −35° C. Other combinations of the wt. % monomer units derived from 1-hexene, 100° C. kinematic viscosity, viscosity index, and pour point either alone or in addition with other properties such as amount of hydrogenated oligomer having less than a specified wt. % of hydrogenated oligomer, having less than a specified number of carbon atoms, and/or the presence or absence of a discernable crystallization above −40° C. for the hydrogenated oligomer composition in the base oil composition (or the lubricant composition) having a nominal 100° C. kinematic viscosity in any range from 80 to 120 cSt are readily apparent from this disclosure. These features for the hydrogenated oligomer composition in the base oil composition (or the lubricant composition) having a nominal 100° C. kinematic viscosity in any range from 80 to 120 cSt are independently described herein and may be utilized in any combination and without limitation to further describe the hydrogenated oligomer composition in the base oil composition (or the lubricant composition) having a nominal 100° C. kinematic viscosity in any range from 80 to 120 cSt.

Referring now to the high viscosity PAO, the high viscosity PAO in the base oil composition (or the lubricant composition) can be described as having a specified 100° C. kinematic viscosity, a specified viscosity index, a specified pour point, comprise monomer units derived from specified monomer(s), have specified wt. % of monomer units derived from specified monomer(s), and/or be substantially free of monomer units derived from specified monomer(s). These features of the high viscosity PAO used in the base oil composition (or lubricant composition) are independently described herein. These independent features can be utilized in any combination, and without limitation to further describe the high viscosity PAO in the base oil composition described herein and can further be utilized in any combination, and without limitation, with the independently described hydrogenated oligomer composition to describe the base oil composition (or the lubricant composition) having a nominal 100° C. kinematic viscosity in any range from 80 to 120 cSt.

Generally, the high viscosity PAO—in the base oil composition (or the lubricant composition) that can have a nominal 100° C. kinematic viscosity in any range from 80 to 120 cSt disclosed herein—can have a 100° C. kinematic viscosity in a range from 75 to 150 cSt. For instance, the high viscosity PAO can have a minimum 100° C. kinematic viscosity of 75, 80, 85, or 90 cSt; alternatively, or additionally, the maximum 100° C. kinematic viscosity of the high viscosity PAO can be 150, 120, 115, or 110 cSt. Generally, the 100° C. kinematic viscosity of the high viscosity PAO can be in a range from any minimum 100° C. kinematic viscosity disclosed herein to any maximum 100° C. kinematic viscosity disclosed herein. Therefore, suitable non-limiting ranges for the 100° C. kinematic viscosity of the high viscosity PAO can include the following ranges: from 75 to 150 cSt, from 75 to 115 cSt, from 80 to 120 cSt, from 80 to 115 cSt, from 80 to 110 cSt, from 85 to 120 cSt, from 85 to 115 cSt, from 85 to 110 cSt, from 90 to 150 cSt, from 90 to 120 cSt, from 90 to 115 cSt, or from 90 to 110 cSt. Other appropriate ranges for the 100° C. kinematic viscosity of the high viscosity PAO are readily apparent from this disclosure.

The high viscosity PAO in the base oil composition (or the lubricant composition) having a nominal 100° C. kinematic viscosity in any range from 80 to 120 cSt disclosed herein can have a viscosity index of from 140 to 300. For instance, the minimum viscosity index of the high viscosity PAO can be at least 140, 145, 150, or 155; alternatively, or additionally, the maximum viscosity index can be 300, 280, 260, or 250. Generally, the viscosity index of the high viscosity PAO can be in a range from any minimum viscosity index disclosed herein to any maximum viscosity index disclosed herein. Therefore, suitable non-limiting ranges for the viscosity index of the high viscosity PAO can include the following ranges: from 140 to 300, from 140 to 260, from 145 to 280, from 145 to 250, from 150 to 300, from 150 to 260, from 155 to 300, from 155 to 280, from 155 to 260, or from 155 to 250. Other appropriate ranges for the viscosity index of the high viscosity PAO are readily apparent from this disclosure.

The pour point of the high viscosity PAO in the base oil composition (or the lubricant composition) having a nominal 100° C. kinematic viscosity in any range from 80 to 120 cSt disclosed herein typically can be less than or equal to −20° C. For instance, the minimum pour point of the high viscosity PAO can be −60, −55, −50, or −48° C.; alternatively, or additionally, the maximum pour point can be −20, −23, −26, or −29° C. Generally, the pour point of the high viscosity PAO can be in a range from any minimum pour point temperature disclosed herein to any maximum pour point temperature disclosed herein. Therefore, suitable non-limiting ranges for the pour point of the high viscosity PAO can include the following ranges: less than −20° C., less than −26° C., less than −29° C., from −20 to −60° C., from −20 to −50° C., from −20 to −48° C., from −23 to −55° C., from −23 to −48° C., from −26 to −60° C., from −26 to −50° C., from −26 to −48° C., from −29 to −60° C., from −29 to −55° C., from −29 to −50° C., or from −29 to −48° C. Other appropriate ranges for the pour point of the high viscosity PAO are readily apparent from this disclosure.

Generally, the high viscosity PAO in the base oil composition (or the lubricant composition) having a nominal 100° C. kinematic viscosity in any range from 80 to 120 cSt disclosed herein can comprise monomer units derived from a $C_8$ to $C_{18}$ normal alpha olefin; alternatively, a $C_8$ to $C_{16}$ normal alpha olefin; or alternatively, 1-octene, 1-decene, 1-dodecene, 1-tetradecene, or any combination thereof. In an embodiment, the high viscosity PAO can comprise monomer units derived from 1-octene, 1-decene, 1-dodecene, or any combination thereof In another embodiment, the high viscosity PAO can comprise monomer units derived from 1-decene, 1-dodecene, 1-tetradecene, or any combination thereof. In yet another embodiment, the high viscosity PAO can comprise comprises monomer units derived from 1-decene, 1-dodecene, or a combination thereof. In still another embodiment, the high viscosity PAO can comprise monomer units derived from 1-octene; alternatively, 1-decene; alternatively, 1-dodecene; or alternatively, 1-tetradecene. Consistent with certain embodiments of this invention, and beneficially, the high viscosity PAO used in the base oil composition (or the lubricant composition) having a nominal 100° C. kinematic viscosity in any range from 80 to 120 cSt disclosed herein can be substantially free of a 1-decene PAO, or substantially free of a predominantly 1-decene PAO. In an embodiment, the high viscosity PAO can contain less than 15 wt. %, less than 10 wt. %, less than 5 wt. %, or less than 1 wt. % of a PAO having at least 80 wt. %, at least 85 wt. %, at least 90 wt. %, at least 92.5 wt. %, at least 95 wt. %, or at least 97.5 wt. % monomer units derived from 1-decene. As an example, the high viscosity PAO can contain less than 15 wt. % of a PAO having at least 80 wt. % monomer units derived from 1-decene. As another example, the high viscosity PAO can contain less than 5 wt. % of a PAO having at least 90 wt. % monomer units derived from 1-decene. As yet another example, the high viscosity PAO can contain less than 1 wt. % of a PAO having at least 95 wt. % monomer units derived from 1-decene.

Also consistent with certain embodiments of this invention, and beneficially, the base oil composition (or the lubricant composition) having a nominal 100° C. kinematic viscosity in any range from 80 to 120 cSt disclosed herein can be substantially free of a 1-decene PAO, or substantially free of a predominantly 1-decene PAO. In an embodiment, the base oil composition (or the lubricant composition) can contain less than 10 wt. %, less than 5 wt. %, less than 2 wt. %, or less than 1 wt. % of a PAO having at least 80 wt. %, at least 85 wt. %, at least 90 wt. %, at least 92.5 wt. %, at least 95 wt. %, or at least 97.5 wt. % monomer units derived from 1-decene. As an example, the base oil composition (or the lubricant composition) can contain less than 10 wt. % of a PAO having at least 80 wt. % monomer units derived from 1-decene. As another example, the base oil composition (or the lubricant composition) can contain less than 5 wt. % of a PAO having at least 90 wt. % monomer units derived from 1-decene. As yet another example, the base oil composition (or the lubricant composition) can contain less than 1 wt. % of a PAO having at least 95 wt. % monomer units derived from 1-decene.

In an embodiment, the hydrogenated oligomer compositions disclosed herein can be used in a variety of compositions or products for a diverse range of applications and industries. For example, the hydrogenated oligomer compositions can be utilized as a lubricant base oil (or a component of a lubricant base oil) for lubricant compositions and/or functional fluid compositions. Exemplary lubricant compositions in which the hydrogenated oligomer compositions can be utilized include, but are not limited to, greases, gearbox oils, engine oils, transmission fluids, and/or drilling fluids. Exemplary functional fluid compositions in which the hydrogenated oligomer compositions can be utilized include, but are not limited to, hydraulic fluids, drilling fluids, coolant fluids, and/or dielectric coolant fluids. In an embodiment, the hydrogenated oligomer compositions described herein can be utilized as the sole base oil for a lubricant composition and/or functional fluid composition. In other embodiments, the hydrogenated oligomer compositions described herein can be combined with one or more other base oils to form a base oil for a lubricant composition and/or functional fluid composition. Additional information on the use of oligomers in lubricant compositions and/or functional fluid compositions can be found in "Synthetic Lubricants and High-Performance Functional Fluids," 2nd Ed., L. Rudnick, ed., Marcel Dekker, Inc., NY (1999).

Additional information on additives used in product formulation can be found in "Lubricants and Lubrications," T. Mang and W. Dresel, eds., Wiley-VCH GmbH, Weinheim (2001).

Formulated lubricant compositions can further include one or more additives. Additives which can be included in a formulated lubricant composition can include, but are not limited to, viscosity index improvers/viscosity modifiers/viscosity improvers, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, friction modifiers, lubricity agents, anti-staining agents, chromophores (dyes), and/or haze inhibitors. Additional information on additives used in product formulations can be found in "Fuels and Lubricants Handbook: Technology, Properties, Performance, and Testing" edited by George E. Totten, Steven R. Westbrook, Rajesh J. Shah, ASTM (2003), ISBN 0-8031-2096-6; Chapter 9 Additives and Additive Chemistry, pp. 199-248, "Lubricants and Related Products," Klamann, Verlag Chemie, Deerfield Beach, Fla., ISBN 0-89573-177-0; "Lubricant Additives" by M. W. Ranney, published by Noyes Data Corporation of Parkridge, N.J. (1973); "Lubricants and Lubrications," T. Mang and W. Dresel, eds., Wiley-VCH GmbH, Weinheim (2001); and "Lubricant Additives", C. V. Smallheer and R. K. Smith, published by the Lezius-Hiles Co. of Cleveland, Ohio (1967).

Viscosity index improvers (also known as viscosity modifiers and viscosity improvers) can provide lubricant compositions and/or functional fluid compositions with high and low temperature operability. These additives can impart shear stability at elevated temperatures and acceptable viscosity at low temperatures. Suitable viscosity index improvers can include high molecular weight hydrocarbons, olefin polymers and copolymers, polyesters, and viscosity index improver dispersants that function as both a viscosity index improver and a dispersant. Viscosity index improvers can have molecular weights ranging from about 10,000 Da to about 1,000,000 Da, from about 20,000 Da to about 500,000 Da, or from about 50,000 Da to about 200,000 Da.

Viscosity index improvers can include polymers and copolymers of methacrylate, butadiene, olefins, or alkylated styrenes. Exemplary viscosity index improvers include, but are not limited to, polyisobutylene, copolymers of ethylene and propylene, hydrogenated block copolymers of styrene and isoprene, polyacrylates (e.g., polymers and/or copolymers of various chain length acrylates), and polymethacrylates (e.g., polymers and/or copolymers of various chain length alkyl methacrylates). Generally, the viscosity index improver can be used in an amount of from 0.01 wt. % to 6 wt. %, from 0.01 to 5 wt. %, or from 0.01 to 4 wt. %, based upon the total weight of the composition.

Dispersants are additives that can be utilized to maintain oxidation products (produced during use of the lubricant composition) in suspension in the lubricant compositions and/or functional fluid compositions to prevent the accumulation of debris that could score bearings, block lubricant pathways, prevent deposit formations, inhibit corrosive wear by neutralizing acidic products (e.g., combustion products), and other types of damage. Dispersants can be ash-containing or ashless in character. Dispersants can include, but are not limited to, alkenylsuccinic acid or anhydride derivatives (e.g., succinimides, succinate esters, or succinate ester amides), phenates, Mannich-Base condensates (e.g., the condensation products of alkylphenols, amines and aldehydes), hydrocarbyl substituted amines, sulfonates, sulfurized phenates, salicylates, naphthenates, stearates, carbamates, thiocarbamates, and phosphorus derivatives in metallic and non-metallic versions. Suitable dispersants can contain a polar group attached to a relatively high molecular weight hydrocarbon chain where the polar group contains at least one element of nitrogen, oxygen, or phosphorus. Patents describing dispersants which can be utilized in the lubricant compositions and/or functional fluid compositions include, but are not limited to, U.S. Pat. Nos. 3,036,003; 3,087,936; 3,172,892; 3,200,107; 3,215,707; 3,219,666; 3,254,025; 3,272,746; 3,275,554; 3,322,670; 3,329,658; 3,316,177; 3,438,757; 3,341,542; 3,413,347; 3,438,757; 3,444,170; 3,449,250; 3,454,555; 3,454,607; 3,519,565; 3,541,012; 3,565,804; 3,630,904; 3,632,511; 3,652,616; 3,666,730; 3,687,849; 3,697,574; 3,702,300; 3,703,536; 3,704,308; 3,725,277; 3,725,480; 3,726,882; 3,751,365; 3,755,433; 3,756,953; 3,787,374; 3,798,165; 3,803,039; 3,822,209; 3,948,800; 4,100,082; 4,234,435; 4,426,305; 4,454,059; 4,767,551; and 5,705,458, among others. Generally, dispersants can be used in an amount from 0.1 wt. % to 20 wt. %, 0.1 wt. % to 15 wt. %, or 0.1 wt. % to 8 wt. %, based upon the total weight of the composition. Detergents are additives that can be utilized to maintain overall cleanliness by keeping sludge, carbon and deposit precursors suspended in the lubricant compositions and/or functional fluid compositions. Many detergents are chemically similar to dispersants. Detergents which can be utilized in the lubricant compositions and/or functional fluid compositions can include the alkali or alkaline earth metal of sulfates, sulfonates, phenates, carboxylates, phosphates, carboxylic acids, and salicylates. For example, suitable detergents can include, but are not limited to, the sulfonated alkylaromatic hydrocarbons, alkyl phenols, sulfurized alkyl phenols treated with an alkaline earth metal hydroxide or oxide (e.g., CaO, $Ca(OH)_2$, BaO, $Ba(OH)_2$, MgO, or $Mg(OH)_2$). Sulfonated alkylaromatic compounds can be prepared from sulfonic acids obtained by sulfonation of $C_9$ to $C_{80}$ (or $C_6$ to $C_{60}$) alkyl substituted aromatic hydrocarbons (having one or more than one alkyl groups) where the alkyl groups independently can be $C_3$ to $C_{70}$ alkyl groups and the aromatic portion can be benzene, toluene, xylene, naphthalene, or biphenyl. Alkyl phenol and/or sulfurized alkyl phenols can have one or more $C_4$ to $C_{30}$ alkyl groups. The detergents utilized in the lubricant compositions and/or functional fluid compositions can be neutral (i.e., produced using only enough alkali or alkaline earth compound to neutralize the sulfonated alkylaromatic compound, alkyl phenol, or sulfurized alkyl phenol) or can be overbased (i.e., produced using more alkali or alkaline earth compound than necessary to neutralize the sulfonated alkylaromatic compound, alkyl phenol, or sulfurized alkyl phenol). Generally, detergents can be used in an amount from 0.01 wt. % to 6.0 wt. %, 0.05 wt. % to 5.0 wt. %, or 0.1 to 4 wt. %, based upon the total weight of the composition.

Defoamants (or anti-foam agents) are additives that can be utilized to retard the formation of stable foam in the lubricant compositions and/or functional fluid compositions. Defoamants which can be utilized in the lubricant compositions and/or functional fluid compositions can include, but are not limited to, silicone compounds (e.g., polysiloxanes, such as silicon oil or polydimethyl siloxane, among others)

and organic polymers. Defoamants can be utilized in conjunction with demulsifiers. Generally, the maximum amount of defoamants can be 1 wt. %, 0.5 wt. %, or 0.1 wt. %, based upon the total weight of the composition.

Antioxidants are additives that can be utilized to retard the oxidative degradation of the base oil(s) in the lubricant compositions and/or functional fluid compositions. Oxidative base oil degradation can produce deposits on metal surfaces, sludge, and/or increase the viscosity of the lubricant composition. Antioxidants which can be utilized in the lubricant compositions and/or functional fluid compositions include, but are not limited to, hindered phenols (ashless); neutral or basic metal salts of hindered phenols; hindered phenolic carboxylic acid (e.g., propionic acid) ester derivatives; bis-hindered phenols; alkylated and non-alkylated aromatic amines; sulfurized alkyl phenols; alkali or alkaline earth metal salts of sulfurized alkyl phenols; copper dihydrocarbyl thio or dithio-phosphates; copper salts of carboxylic acids (natural or synthetic); and copper salts of dithiacarbamates, dithiocarbamates, sulphonates, phenates, acetylacetonates and alkenyl succinic acids or anhydrides (neutral, basic or acidic). Patents describing antioxidants which can be utilized in the lubricant compositions and/or functional fluid compositions include, but are not limited to, U.S. Pat. Nos. 4,798,684 and 5,084,197. Generally, the antioxidants can be used in an amount from 0.01 wt. % to 5 wt. %, from 0.01 to 2.5 wt. %, or from 0.01 wt. % to 1.5 wt. %, based upon the total weight of the composition.

Anti-wear additives and extreme pressure additives are compounds that can be utilized to reduce friction and wear of metal parts of the base oil(s) in the lubricant compositions and/or functional fluid compositions. Anti-wear additives and extreme pressure additives which can be utilized in the lubricant compositions and/or functional fluid compositions include, but are not limited to, metal alkylthiophosphates (e.g., a zinc alkylthiophosphonate having a $C_1$ to $C_{18}$ alkyl group), metal dialkyldithiophosphates (e.g., a zinc alkylthiophosphonate having $C_1$ to $C_{18}$ alkyl groups), sulfurized $C_3$ to $C_{30}$ aliphatic or arylaliphatic hydrocarbon olefins (acyclic or cyclic), polysulfides of thiophosphorus acids, polysulfides of thiophosphorus acid esters, phosphorothionyl disulfides, alkylthiocarbamoyl compounds (e.g., bis(dibutyl)thiocarbamoyl) in combination with a molybdenum compound (e.g., oxymolybdenum diisopropylphosphorodithioate sulfide) and a phosphorus ester (e.g., dibutyl hydrogen phosphite, for example), thiocarbamates, thiocarbamate/molybdenum complexes (e.g., moly-sulfur alkyl dithiocarbamate trimer complexes), and/or glycerol ester (e.g., mono-, di-, and tri-oleates, mono-palmitates and mono-myristates). Patents describing anti-wear additives and/or extreme pressure additives which can be utilized in the lubricant compositions and/or functional fluid compositions include, but are not limited to, U.S. Pat. Nos. 2,443,264; 2,471,115; 2,526,497; 2,591,577; 3,770,854; 4,501,678; 4,941,984; 5,034,141; 5,034,142; 5,084,197; and 5,693,598. Generally, the total amount of anti-wear additives and extreme pressure additives used in the lubricant compositions and/or functional fluid compositions can be from 0.01 wt. % to 6 wt. %, from 0.01 to 5 wt. %, or from 0.01 wt. % to 4 wt. %, based upon the total weight of the composition.

Anti-rust additives are additives that can protect lubricated metal surfaces against chemical attack by water or other contaminants. Anti-rust additives can function by 1) wetting the metal surface with a film of oil, 2) absorbing water into a water-in-oil emulsion, and/or 3) adhering to the metal to form a non-reactive surface, among other potential modes of function. Anti-rust additives which can be utilized in the lubricant compositions and/or functional fluid compositions include, but are not limited to, zinc dithiophosphates, metal phenolates, basic metal sulfonates, fatty acids, and amines. Generally, the amount of anti-rust additives used in the lubricant compositions and/or functional fluid compositions can be from 0.01 wt. % to 5 wt. %, from 0.01 wt. % to 2.5 wt. %, or from 0.01 wt. % to 1.5 wt. %, based upon the total weight of the composition.

Corrosion inhibitors are additives that can reduce the degradation of metallic parts that are in contact with the lubricant compositions and/or functional fluid compositions. Corrosion inhibitors which can be utilized in the lubricant compositions and/or functional fluid compositions include, but are not limited to, thiadiazoles and triazoles. Patents describing corrosion inhibitors which can be utilized in the lubricant compositions and/or functional fluid compositions include, but are not limited to, U.S. Pat. Nos. 2,719,125; 2,719,126; and 3,087,932. Generally, the amount of corrosion inhibitors used in the lubricant compositions and/or functional fluid compositions can be from 0.01 wt. % to 5 wt. %, from 0.01 wt. % to 2.5 wt. %, or from 0.01 wt. % to 1.5 wt. %, based upon the total weight of the composition.

Pour point depressants are additives that can reduce the minimum temperature at which the lubricant compositions and/or functional fluid compositions will flow or can be poured. Pour point depressants which can be utilized in the lubricant compositions and/or functional fluid compositions include, but are not limited to, polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Patents describing pour point depressants which can be utilized in the lubricant compositions and/or functional fluid compositions include, but are not limited to, U.S. Pat. Nos. 1,815,022; 2,015,748; 2,191,498; 2,387,501; 2,655,479; 2,666,746; 2,721,877; 2,721,878; and 3,250,715. Generally, the amount of the pour point depressant used in the lubricant compositions and/or functional fluid compositions can be from 0.01 wt. % to 5 wt. %, from 0.01 wt. % to 2.5 wt. %, or from 0.01 wt. % to 1.5 wt. %, based upon the total weight of the composition.

Seal compatibility additives are compounds that can swell elastomeric seals and can function by causing a chemical reaction in the fluid or a physical change in the seal elastomer. Seal compatibility additives which can be utilized in the lubricant compositions and/or functional fluid compositions include, but are not limited to, organic phosphates, aromatic esters, aromatic hydrocarbons, esters (e.g., butylbenzyl phthalate), and polybutenyl succinic anhydride. Generally, the amount of the seal compatibility additive used in the lubricant composition and/or functional fluid compositions can be from 0.01 wt. % to 3 wt. %, from 0.01 wt. % to 2.5 wt. %, or from 0.01 wt. % to 2 wt. %, based upon the total weight of the composition.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Kinematic viscosities at 100° C. and 40° C. were determined in accordance with ASTM D7042-04 (Stabinder viscometer method) or ASTM D445-06 (capillary tube method) at the respective temperatures, and the results are reported in centistokes (cSt). The viscosity index was determined in accordance with ASTM D2270-10e1, using the tables provided therein for viscosity data determined at 100° C. and 40° C. Pour point is a measurement of the temperature at which the sample will begin to flow under carefully controlled conditions. Pour point was determined in accordance with ASTM D97-04 or ASTM D5950-02(2007) (automatic tilt method), and the results are reported in ° C.

Fluorided silica-coated alumina (F-SCA) was prepared as follows. Alumina A from W.R. Grace having a surface area of 300 m²/g, a pore volume of 1.2 mL/g, and an average particle size of 100 microns, was first calcined in dry air for 6 hours at 600° C., then cooled to ambient temperature, followed by contacting with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina (F-SCA) was collected and stored under dry nitrogen, and was used without exposure to the atmosphere.

Fluorided silica-alumina (F-SiAl) was prepared as follows. A silica-alumina was obtained from W.R. Grace Company containing 13% alumina by weight and having a surface area of 400 m²/g, a pore volume of 1.2 mL/g, and an average particle size of 70 microns. Approximately 100 grams of this material were impregnated with a solution containing about 200 mL of water and about 10 grams of ammonium hydrogen fluoride, resulting in a damp powder having the consistency of wet sand. After drying, the fluorided silica-alumina was calcined for 3 hours at 450° C. in dry air. Afterward, the fluorided silica-alumina (F-SiAl) was collected and stored under dry nitrogen, and was used without exposure to the atmosphere.

The metallocene compound (MET 1) used in the oligomerization experiments was (n-butyl)$_2$-Si bridged bis-cyclopentadienyl zirconium dichloride:

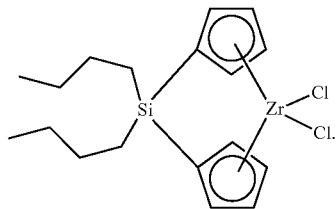

MET 1

Examples 1-5

A slurry of 500 mg of the chemically-treated solid oxide (F-SCA or F-SiAl), 1.26 mmol of triisobutylaluminum (1 molar solution in heptanes), and 1.2 mL of a 1 mg/mL solution of metallocene MET 1 in toluene were charged to a 500 mL flask, followed by 400 mL of 1-hexene. The flask was then heated to the desired reaction temperature (45° C. to 65° C.; Examples 1-5), and the reaction allowed to proceed, with stirring at 1000 rpm, for 5 to 18 hours at ambient pressure. After cooling to room temperature, the oligomer product was collected and filtered to remove the chemically-treated solid oxide. The filtrate was then subjected to vacuum at <2 ton (<0.27 kPa) and 135° C., with stirring, for at least 15 minutes to remove a portion of unreacted 1-hexene and light 1-hexene oligomers, resulting in a heavy 1-hexene oligomer product.

The kinematic viscosity (KV) of each heavy 1-hexene oligomer product at 100° C. was determined using the method indicated herein. Table I summarizes the 100° C. kinematic viscosity as a function of the oligomerization temperature and the chemically-treated solid oxide used. Unexpectedly, the 100° C. kinematic viscosity decreased as the oligomerization temperature increased, regardless of the chemically-treated solid oxide used, and the heavy 1-hexene oligomer products produced using F-SCA had significantly lower viscosities than those produced using F-SiAl.

Examples 6-17

The heavy oligomer products of Examples 6-12 were prepared in a similar manner to Examples 1-5. The 100° C. kinematic viscosity (KV) and viscosity index of each heavy 1-hexene oligomer product were determined using the methods indicated herein. Table II summarizes the viscosity index of the heavy 1-hexene oligomer products of Examples 6-12 at various 100° C. kinematic viscosities, and as a function of the chemically-treated solid oxide used. In Table II, Example 13 was a 100 cSt 1-decene PAO, and Example 14 was a 100 cSt 1-octene PAO.

As shown by Examples 6-10, as the 100° C. kinematic viscosity increases, generally the viscosity index also increased. Examples 9-10 demonstrate a slightly lower viscosity index as compared to Examples 13-14. Using blends of F-SCA and F-SiAl in Examples 11-12 resulted in high viscosity indices along with high 100° C. kinematic viscosities.

Table III summarizes the 100° C. kinematic viscosity and the viscosity index of the heavy 1-hexene oligomer products of Examples 9-12 and 15-17 as a function of the relative amount of chemically-treated solid oxide used. Examples 15-17 were produced in a similar manner to Examples 1-5. Unexpectedly, the use of F-SiAl—even at only 25 wt. % (with 75 wt. % F-SCA)—resulted in significant increases in the 100° C. kinematic viscosity.

Examples 18-27

Example 18 was a heavy 1-hexene oligomer product produced as described above for Example 4, using F-SCA. Examples 19-20 were 1-octene and 1-decene oligomer products, respectively, produced in a similar manner to Example 4 using F-SCA. Example 21 was a commercial 100 cSt 1-octene mPAO, while Example 22 was a commercial 100 cSt 1-decene PAO. Example 23 was a 50:50 blend (by weight) of Example 18 and Example 21.

Example 24 was a commercial 40 cSt 1-octene mPAO, while Example 25 was a commercial 40 cSt 1-decene PAO. Example 26 was a 3:1 blend (by weight) of Example 18 and PAO-5 (a 1-dodecene trimer having a kinematic viscosity at 100° C. of 5 cSt). Example 27 was a 3:1 blend (by weight) of Example 18 and a $C_{14}$ dimer having a kinematic viscosity at 100° C. of 4.2 cSt.

Table IV summarizes the 100° C. kinematic viscosity (KV), the 40° C. kinematic viscosity (KV), the viscosity index, and the pour point of the lubricant compositions of Examples 18-27. As shown in Table IV, and unexpectedly, Example 23 demonstrates that a nominal 100 cSt lubricant composition can be produced with properties equivalent to or better than that of a traditional 100 cSt 1-decene PAO, via a blend using the heavy 1-hexene oligomer product of Example 18. Similarly, and also quite surprisingly, Examples 26-27 demonstrate that nominal 40 cSt lubricant compositions can be produced with properties equivalent to or better than that of a traditional 40 cSt 1-decene PAO, via blends using the heavy 1-hexene oligomer product of Example 18. Thus, lubricant compositions having comparable or superior properties (e.g., higher viscosity index and lower pour point) to 1-decene PAO products can be beneficially produced without using 1-decene.

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1. A hydrogenated oligomer composition comprising at least 80 wt. % monomer units derived from 1-hexene and having a 100° C. kinematic viscosity in a range from 75 to 150 cSt, a viscosity index in a range from 150 to 180, and a pour point in a range from −20 to −40° C.

Embodiment 2. The hydrogenated oligomer composition defined in embodiment 1, wherein the hydrogenated oligomer composition has a 100° C. kinematic viscosity in any range of 100° C. kinematic viscosities disclosed herein, e.g., from 80 to 140 cSt, from 80 to 125 cSt, from 85 to 115 cSt, from 90 to 110 cSt, etc.

Embodiment 3. The hydrogenated oligomer composition defined in embodiment 1 or 2, wherein the hydrogenated oligomer composition has a viscosity index in any range of viscosity indices disclosed herein, e.g., from 150 to 175, from 150 to 170, from 155 to 165, etc.

Embodiment 4. The hydrogenated oligomer composition defined in any one of embodiments 1-3, wherein the hydrogenated oligomer composition has a pour point in any range of pour points disclosed herein, e.g., from −20 to −35° C., from −25 to −40° C., from −25 to −35° C., etc.

Embodiment 5. The hydrogenated oligomer composition defined in any one of embodiments 1-4, wherein the hydrogenated oligomer composition has a 40° C. kinematic viscosity in any range of 40° C. kinematic viscosities disclosed herein, e.g., from 750 to 2800 cSt, from 900 to 2500 cSt, from 1000 to 2000 cSt, from 1200 to 1600 cSt, etc.

Embodiment 6. The hydrogenated oligomer composition defined in any one of embodiments 1-5, wherein the hydrogenated oligomer composition comprises any amount of monomer units derived from 1-hexene disclosed herein, e.g., at least 80 wt. %, at least 90 wt. %, at least 95 wt. %, at least 97 wt. %, at least 98 wt. %, at least 98.5 wt. %, at least 99 wt. %, etc.

Embodiment 7. The hydrogenated oligomer composition defined in any one of embodiments 1-6, wherein the hydrogenated oligomer composition comprises less than any amount of hydrogenated oligomers having 24 carbon atoms or less, 30 carbon atoms or less, or 36 carbon atoms or less,

TABLE I

| Example | Temperature (° C.) | KV at 100° C. using F-SCA (cSt) | KV at 100° C. using F-SiAl (cSt) |
|---|---|---|---|
| 1 | 45 | 191 | — |
| 2 | 50 | 172 | 494 |
| 3 | 55 | 152 | — |
| 4 | 60 | 105 | 371 |
| 5 | 65 | 81 | 307 |

TABLE II

| Example | KV at 100° C. (cSt) | Viscosity Index | Chemically-Treated Solid Oxide |
|---|---|---|---|
| 6 | 191 | 168 | F-SCA |
| 7 | 172 | 167 | F-SCA |
| 8 | 152 | 157 | F-SCA |
| 9 | 104 | 160 | F-SCA |
| 10 | 106 | 160 | F-SCA |
| 11 | 315 | 178 | F-SCA:F-SiAl = 3:1 |
| 12 | 456 | 186 | F-SCA:F-SiAl = 1:1 |
| 13 | 100 | 170 | N/A |
| 14 | 100 | 194 | N/A |

TABLE III

| Example | F-SCA (wt. %) | F-SiAl (wt. %) | KV at 100° C. (cSt) | Viscosity Index |
|---|---|---|---|---|
| 9 | 100 | 0 | 104 | 160 |
| 10 | 100 | 0 | 106 | 160 |
| 11 | 75 | 25 | 315 | 178 |
| 12 | 50 | 50 | 456 | 186 |
| 15 | 50 | 50 | 360 | 179 |
| 16 | 25 | 75 | 415 | 173 |
| 17 | 0 | 100 | 371 | 181 |

TABLE IV

| | 18 Nominal 100 cSt $C_6$ oligomer | 19 Nominal 100 cSt $C_8$ oligomer | 20 Nominal 100 cSt $C_{10}$ oligomer | 21 100 cSt $C_8$ mPAO | 22 100 cSt $C_{10}$ PAO | 23 100 cSt Blend of Ex 18 + Ex 21 | 24 40 cSt $C_8$ mPAO | 25 40 cSt $C_{10}$ PAO | 26 40 cSt Blend of Ex 18 + PAO 5 | 27 40 cSt Blend of Ex 18 + $C_{14}$ dimer |
|---|---|---|---|---|---|---|---|---|---|---|
| KV at 100° C. (cSt) | 105 | 114 | 91 | 100 | 100 | 100 | 40 | 40 | 42 | 41.5 |
| KV at 40° C. (cSt) | 1460 | — | — | 1014 | 1231 | 1206 | 341 | 395 | 412 | 395 |
| Viscosity Index | 160 | 203 | 212 | 194 | 170 | 173 | 170 | 147 | 156 | 157.5 |
| Pour Point (° C.) | −30 | −38 | −44 | −44 | −30 | −35 | −50 | −36 | −44 | — | disclosed herein, e.g., less than 5 wt. %, less than 3 wt. %, less than 1 wt. %, less than 0.5 wt. %, less than 0.25 wt. %, less than 0.1 wt. %, etc.

Embodiment 8. The hydrogenated oligomer composition defined in any one of embodiments 1-7, wherein the hydrogenated oligomer composition has no discernable crystallization according to DSC using ASTM D3418-97.

Embodiment 9. A base oil composition (or a lubricant composition) comprising the hydrogenated oligomer composition defined in any one of embodiments 1-8.

Embodiment 10. A base oil composition (or a lubricant composition) comprising:
(i) the hydrogenated oligomer composition defined in any one of embodiments 1-8; and
(ii) a low viscosity PAO having a 100° C. kinematic viscosity in a range from 1 to 20 cSt;
wherein a weight ratio of the hydrogenated oligomer composition:low viscosity PAO is in a range from 25:75 to 90:10; and
wherein the base oil composition (or the lubricant composition) has a 100° C. kinematic viscosity in a range from 30 to 50 cSt.

Embodiment 11. The base oil composition (or the lubricant composition) defined in embodiment 10, wherein the base oil composition (or the lubricant composition) has a 100° C. kinematic viscosity in any range of 100° C. kinematic viscosities disclosed herein, e.g., from 30 to 45 cSt, from 35 to 50 cSt, from 35 to 45 cSt, from 37 to 43 cSt, etc.

Embodiment 12. The base oil composition (or the lubricant composition) defined in embodiment 10 or 11, wherein the base oil composition (or the lubricant composition) has a viscosity index in any range of viscosity indices disclosed herein, e.g., from 130 to 180, from 140 to 170, from 140 to 165, etc.

Embodiment 13. The base oil composition (or the lubricant composition) defined in any one of embodiments 10-12, wherein the base oil composition (or the lubricant composition) has a pour point in any range of pour points disclosed herein, e.g., less than −25° C., less than −30° C., less than −32° C., from −25 to −60° C., from −30 to −55° C., from −30 to −50° C., from −32 to −48° C., etc.

Embodiment 14. The base oil composition (or the lubricant composition) defined in any one of embodiments 10-13, wherein the base oil composition (or the lubricant composition) has a 40° C. kinematic viscosity in any range of 40° C. kinematic viscosities disclosed herein, e.g., from 300 to 500 cSt, from 350 to 500 cSt, from 350 to 450 cSt, from 375 to 425 cSt, etc.

Embodiment 15. The base oil composition (or the lubricant composition) defined in any one of embodiments 10-14, wherein the weight ratio of the hydrogenated oligomer composition:low viscosity PAO is in any range of weight ratios disclosed herein, e.g., from 35:65 to 80:20, from 35:65 to 75:25, from 50:50 to 75:25, etc.

Embodiment 16. The base oil composition (or the lubricant composition) defined in any one of embodiments 10-15, wherein the low viscosity PAO has a 100° C. kinematic viscosity in any range of 100° C. kinematic viscosities disclosed herein, e.g., from 2 to 20 cSt, from 1 to 15 cSt, from 2 to 12 cSt, from 2 to 10 cSt, etc.

Embodiment 17. The base oil composition (or the lubricant composition) defined in any one of embodiments 10-16, wherein the low viscosity PAO has a viscosity index in any range of viscosity indices disclosed herein, e.g., from 90 to 200, from 95 to 180, from 95 to 160, from 100 to 160, from 110 to 160, from 120 to 155, etc.

Embodiment 18. The base oil composition (or the lubricant composition) defined in any one of embodiments 10-17, wherein the low viscosity PAO has a pour point in any range of pour points disclosed herein, e.g., less than −20° C., less than −26° C., less than −32° C., from −20 to −85° C., from −23 to −80° C., from −26 to −75° C., from −29 to −75° C., from −32 to −75° C., etc.

Embodiment 19. The base oil composition (or the lubricant composition) defined in any one of embodiments 10-18, wherein the low viscosity PAO comprises monomer units derived from a $C_6$ to $C_{18}$ normal alpha olefin; or alternatively, 1-octene, 1-decene, 1-dodecene, 1-tetradecene, or any combination thereof.

Embodiment 20. The base oil composition (or the lubricant composition) defined in any one of embodiments 10-19, wherein the low viscosity PAO comprises less than any maximum amount (e.g., less than 15 wt. %, less than 10 wt. %, less than 5 wt. %, less than 1 wt. %, etc.) of a PAO comprising at least 80 wt. %, at least 85 wt. %, at least 90 wt. %, at least 92.5 wt. %, at least 95 wt. %, or at least 97.5 wt. %, monomer units derived from 1-decene.

Embodiment 21. The base oil composition (or the lubricant composition) defined in any one of embodiments 10-20, wherein the base oil composition (or the lubricant composition) comprises less than any maximum amount (e.g., less than 10 wt. %, less than 5 wt. %, less than 2 wt. %, less than 1 wt. %, etc.) of a PAO comprising at least 80 wt. %, at least 85 wt. %, at least 90 wt. %, at least 92.5 wt. %, at least 95 wt. %, or at least 97.5 wt. %, of monomer units derived from 1-decene.

Embodiment 22. A base oil composition (or a lubricant composition) comprising:
(i) the hydrogenated oligomer composition defined in any one of embodiments 1-8; and
(ii) a high viscosity PAO having a 100° C. kinematic viscosity in a range from 75 to 150 cSt;
wherein a weight ratio of the hydrogenated oligomer composition:high viscosity PAO is in a range from 25:75 to 80:20; and
wherein the base oil composition (or the lubricant composition) has a 100° C. kinematic viscosity in a range from 80 to 120 cSt.

Embodiment 23. The base oil composition (or the lubricant composition) defined in embodiment 22, wherein the base oil composition (or the lubricant composition) has a 100° C. kinematic viscosity in any range of 100° C. kinematic viscosities disclosed herein, e.g., from 80 to 115 cSt, from 85 to 120 cSt, from 85 to 115 cSt, from 90 to 110 cSt, etc.

Embodiment 24. The base oil composition (or the lubricant composition) defined in embodiments 22 or 23, wherein the base oil composition (or the lubricant composition) has a viscosity index in any range of viscosity indices disclosed herein, e.g., from 160 to 200, from 160 to 190, from 165 to 180, etc.

Embodiment 25. The base oil composition (or the lubricant composition) defined in any one of embodiments 22-24, wherein the base oil composition (or the lubricant composition) has a pour point in any range of pour points disclosed herein, e.g., from −25 to −50° C., from −25 to −45° C., from −28 to −38° C., etc.

Embodiment 26. The base oil composition (or the lubricant composition) defined in any one of embodiments 22-25, wherein the base oil composition (or the lubricant composition) has a 40° C. kinematic viscosity in any range of 40°

C. kinematic viscosities disclosed herein, e.g., from 800 to 1800 cSt, from 900 to 1500 cSt, from 1000 to 1400 cSt, from 1100 to 1300 cSt, etc.

Embodiment 27. The base oil composition (or the lubricant composition) defined in any one of embodiments 22-26, wherein the weight ratio of the hydrogenated oligomer composition:high viscosity PAO is in any range of weight ratios disclosed herein, e.g., from 35:65 to 80:20, from 35:65 to 65:35, from 40:60 to 60:40, etc.

Embodiment 28. The base oil composition (or the lubricant composition) defined in any one of embodiments 22-27, wherein the high viscosity PAO has a 100° C. kinematic viscosity in any range of 100° C. kinematic viscosities disclosed herein, e.g., from 80 to 115 cSt, from 85 to 120 cSt, from 85 to 115 cSt, from 90 to 110 cSt, etc.

Embodiment 29. The base oil composition (or the lubricant composition) defined in any one of embodiments 22-28, wherein the high viscosity PAO has a viscosity index in any range of viscosity indices disclosed herein, e.g., at least 140, at least 145, at least, at least, from 140 to 300, from 145 to 280, from 150 to 260, from 155 to 250, etc.

Embodiment 30. The base oil composition (or the lubricant composition) defined in any one of embodiments 22-29, wherein the high viscosity PAO has a pour point in any range of pour points disclosed herein, e.g., less than −20° C., less than −29° C., from −20 to −60° C., from −23 to −55° C., from −26 to −50° C., from −29 to −48° C., etc.

Embodiment 31. The base oil composition (or the lubricant composition) defined in any one of embodiments 22-30, wherein the high viscosity PAO comprises monomer units derived from a $C_6$ to $C_{18}$ normal alpha olefin; or alternatively, 1-octene, 1-decene, 1-dodecene, 1-tetradecene, or any combination thereof.

Embodiment 32. The base oil composition (or the lubricant composition) defined in any one of embodiments 22-31, wherein the high viscosity PAO comprises less than any maximum amount (e.g., less than 15 wt. %, less than 10 wt. %, less than 5 wt. %, less than 1 wt. %, etc.) of a PAO comprising at least 80 wt. %, at least 85 wt. %, at least 90 wt. %, at least 92.5 wt. %, at least 95 wt. %, or at least 97.5 wt. %, monomer units derived from 1-decene.

Embodiment 33. The base oil composition (or the lubricant composition) defined in any one of embodiments 22-32, wherein the base oil composition (or the lubricant composition) comprises less than any maximum amount (e.g., less than 10 wt. %, less than 5 wt. %, less than 2 wt. %, less than 1 wt. %, etc.) of a PAO comprising at least 80 wt. %, at least 85 wt. %, at least 90 wt. %, at least 92.5 wt. %, at least 95 wt. %, or at least 97.5 wt. %, of monomer units derived from 1-decene.

Embodiment 34. The lubricant composition of any one of embodiments 9-32, further comprising a viscosity index improver, a viscosity modifier, a viscosity improver, a dispersant, a detergent, a friction modifier, a traction improving additive, a demulsifier, a defoamant, an antioxidant, an anti-wear additive, a non-metallic extreme pressure additive (e.g., a phosphorus, a non-phosphorus, a sulfur-containing, and/or a non-sulfur non-metallic extreme-pressure additive), a metallic extreme pressure additive (e.g., a phosphorus, a non-phosphorus, a sulfur-containing, and/or a non-sulfur metallic extreme-pressure additive), an anti-rust additive, a corrosion inhibitor, a metal deactivator, an anti-seizure agent, a pour point depressant, a wax modifier, a seal compatibility agent, a friction modifier, a lubricity agent, an anti-staining agent, a chromophore, a haze inhibitor, or any combination thereof.

Embodiment 35. A process comprising:
(a) contacting an olefin feedstock comprising at least 80 wt. % 1-hexene with a catalyst system comprising (i) a metallocene compound, (ii) a chemically treated solid oxide, and (iii) optionally, an organoaluminum compound;
(b) forming an oligomer product under oligomerization conditions;
(c) isolating a heavy oligomer product by removing at least a portion of unreacted 1-hexene and light 1-hexene oligomers from the oligomer product using one or more separations steps; and
(d) hydrogenating the heavy oligomer product to produce the hydrogenated oligomer composition defined in any one of embodiments 1-8.

Embodiment 36. The process defined in embodiment 35, wherein the chemically-treated solid oxide comprises a solid oxide and an electron-withdrawing anion, wherein the solid oxide comprises any solid oxide disclosed herein, e.g., silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion comprises any electron-withdrawing anion disclosed herein, e.g., sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Embodiment 37. The process defined in embodiment 35 or 36, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Embodiment 38. The process defined in embodiment 35 or 36, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Embodiment 39. The process defined in embodiment 35 or 36, wherein the chemically-treated solid oxide comprises fluorided silica-alumina.

Embodiment 40. The process defined in embodiment 35 or 36, wherein the chemically-treated solid oxide comprises fluorided silica-coated alumina.

Embodiment 41. The process defined in embodiment 35 or 36, wherein the chemically-treated solid oxide comprises sulfated alumina.

Embodiment 42. The process defined in embodiment 35 or 36, wherein the chemically-treated solid oxide comprises a fluorided solid oxide, a sulfated solid oxide, or any combination thereof.

Embodiment 43. The process defined in any one of embodiments 35-42, wherein the catalyst system comprises any suitable metallocene compound or any metallocene compound disclosed herein.

Embodiment 44. The process defined in any one of embodiments 35-43, wherein the metallocene compound comprises a bridged zirconium or hafnium based metallocene compound.

Embodiment 45. The process defined in any one of embodiments 35-43, wherein the metallocene compound comprises a bridged zirconium or hafnium based metallocene with a carbon bridging atom or a silicon bridging atom.

Embodiment 46. The process defined in any one of embodiments 35-43, wherein the metallocene compound comprises a bridged zirconium based metallocene with a cyclopentadienyl group and a carbon bridging atom or a silicon bridging atom.

Embodiment 47. The process defined in any one of embodiments 35-43, wherein the metallocene compound comprises a bridged zirconium based metallocene with two cyclopentadienyl groups and a carbon bridging atom or a silicon bridging atom.

Embodiment 48. The process defined in any one of embodiments 35-43, wherein the metallocene compound comprises an unbridged zirconium or hafnium based metallocene compound containing two cyclopentadienyl groups, two indenyl groups, or a cyclopentadienyl group and an indenyl group.

Embodiment 49. The process defined in any one of embodiments 35-43, wherein the metallocene compound comprises an unbridged zirconium or hafnium based metallocene compound containing two cyclopentadienyl groups.

Embodiment 50. The process defined in any one of embodiments 35-43, wherein the metallocene compound comprises an unbridged zirconium based metallocene compound containing two cyclopentadienyl groups.

Embodiment 51. The process defined in embodiment 49 or 50, wherein the cyclopentadienyl groups are alkyl-substituted cyclopentadienyl groups.

Embodiment 52. The process defined in any one of embodiments 35-43, wherein the metallocene compound comprises an unbridged zirconium or hafnium based metallocene compound containing a cyclopentadienyl group and an indenyl group.

Embodiment 53. The process defined in any one of embodiments 35-43, wherein the metallocene compound comprises an unbridged zirconium based metallocene compound containing a cyclopentadienyl group and an indenyl group.

Embodiment 54. The process defined in any one of embodiments 35-43, wherein the metallocene compound comprises an unbridged zirconium based metallocene compound containing a cyclopentadienyl group and an indenyl group with an alkenyl substituent.

Embodiment 55. The process defined in any one of embodiments 35-54, wherein the catalyst system comprises an organoaluminum compound.

Embodiment 56. The process defined in embodiment 55, wherein the organoaluminum compound comprises any trialkylaluminum compound disclosed herein, e.g., trimethylaluminum, triethylaluminum, triisobutylaluminum, etc., or combinations thereof.

Embodiment 57. The process defined in any one of embodiments 35-56, wherein the catalyst system is substantially free of aluminoxane compounds, organoboron or organoborate compounds, ionizing ionic compounds, or combinations thereof.

Embodiment 58. The process defined in any one of embodiments 35-57, wherein the catalyst system is produced by a process comprising contacting, in any order, the metallocene compound, the chemically-treated solid oxide, and the organoaluminum compound.

Embodiment 59. The process defined in any one of embodiments 35-58, wherein a weight ratio of the chemically-treated solid oxide to the metallocene compound is in any range of weight ratios disclosed herein, e.g., from 20:1 to 1500:1, from 50:1 to 1500:1, from 50:1 to 1000:1, from 50:1 to 800:1, from 60:1 to 800:1, from 60:1 to 600:1, from 70:1 to 600:1, from 70:1 to 500:1, etc.

Embodiment 60. The process defined in any one of embodiments 35-59, wherein a molar ratio of aluminum of the organoaluminum compound to transition metal of the metallocene compound is in any range of molar ratios disclosed herein, e.g., from 5:1 to 5000:1, from 5:1 to 1000:1, from 5:1 to 250:1, from 10:1 to 150:1, etc.

Embodiment 61. The process defined in any one of embodiments 35-60, wherein a molar ratio of 1-hexene to the metallocene compound is in any range of molar ratios disclosed herein, e.g., from $1\times10^3$:1 to $1\times10^9$:1, from $1\times10^4$:1 to $1\times10^8$:1, from $1\times10^5$:1 to $1\times10^7$:1, from $1\times10^5$:1 to $1\times10^6$:1, etc.

Embodiment 62. The process defined in any one of embodiments 35-61, wherein the oligomerization conditions comprise an oligomerization temperature in any oligomerization temperature range disclosed herein, e.g., from 0° C. to 165° C., from 20° C. to 160° C., from 40° C. to 160° C., from 20° C. to 100° C., from 20° C. to 80° C., from 35° C. to 75° C., from 40° C. to 70° C., etc.

Embodiment 63. The process defined in any one of embodiments 35-62, wherein the oligomerization conditions comprise a reaction pressure in any range disclosed herein, e.g., from 50 psig (344 kPa) to 4,000 psig (27.6 MPa), from 100 psig (689 kPa) to 3,000 psig (20.9 MPa), from 200 psig (1.4 MPa) to 2,000 psig (13.8 MPa), from 250 psig (1.5 MPa) to 1,500 psig (10.3 MPa), etc.

Embodiment 64. The process defined in any one of embodiments 35-63, wherein the oligomer product is formed in the presence of hydrogen.

Embodiment 65. The process defined in embodiment 64, wherein the oligomer product is formed at a hydrogen partial pressure in any range disclosed herein, e.g., from 1 psig (6.9 kPa) to 2000 psig (13.8 MPa), from 5 psig (34 kPa) to 1500 psig (10.3 MPa), from 10 psig (69 kPa) to 1000 psig (6.9 MPa), from 10 psig (69 kPa) to 500 psig (3.5 MPa), from 25 psig (172 kPa) to 500 psig (3.4 MPa), etc.

Embodiment 66. The process defined in any one of embodiments 35-63, wherein the oligomer product is formed in the substantial absence of hydrogen (e.g., no added hydrogen).

Embodiment 67. The process defined in any one of embodiments 35-66, wherein the activity of the catalyst system is at least 25,000, at least 30,000, at least 35,000, or at least 40,000 grams of oligomer product per gram of metallocene compound per hour.

Embodiment 68. The process defined in any one of embodiments 35-67, wherein the oligomer product is formed in a reaction system comprising a fixed bed reactor, a stirred tank reactor, a plug flow reactor, a loop slurry reactor, or a combination thereof.

Embodiment 69. The process defined in any one of embodiments 35-68, wherein the one of more separations steps comprise any suitable technique or any technique disclosed herein, e.g., a flash process, a distillation process, etc., or any combination thereof.

Embodiment 70. The process defined in any one of embodiments 35-69, wherein the process further comprises a step of deactivating the catalyst system using any suitable technique or any technique disclosed herein.

Embodiment 71. The process defined in any one of embodiments 35-70, wherein the process further comprises a step of separating the oligomer product from the catalyst system or deactivated catalyst system, and the one or more separations steps comprise any suitable technique or any technique disclosed herein, e.g., filtration.

Embodiment 72. The process defined in any one of embodiments 35-71, wherein hydrogenating the heavy oligomer product comprises any suitable hydrogenation technique or any hydrogenation technique disclosed herein.

Embodiment 73. The process defined in any one of embodiments 35-72, wherein the hydrogenated oligomer composition comprises:
i) less than 0.5 wt. % hydrogenated monomer, and
ii) less than 1 wt. % hydrogenated oligomers having 24 carbon atoms or less.

Embodiment 74. The process defined in any one of embodiments 35-73, wherein the hydrogenated oligomer composition comprises:
i) less than 0.2 wt. % hydrogenated monomer, and
ii) less than 0.5 wt. % hydrogenated oligomers having 24 carbon atoms or less.

We claim:

1. A base oil or lubricant composition comprising:
(i) a hydrogenated oligomer composition comprising at least 80 wt. % monomer units derived from 1-hexene, and characterized by a 100° C. kinematic viscosity in a range from 75 to 150 cSt, a viscosity index in a range from 150 to 180, and a pour point in a range from −20 to −40° C.; and
(ii) a low viscosity PAO having a 100° C. kinematic viscosity in a range from 1 to 20 cSt;
wherein a weight ratio of the hydrogenated oligomer composition:low viscosity PAO is in a range from 25:75 to 90:10; and
wherein the base oil or lubricant composition has a 100° C. kinematic viscosity in a range from 30 to 50 cSt.

2. The base oil or lubricant composition of claim 1, wherein:
the hydrogenated oligomer composition comprises at least 98 wt. % monomer units derived from 1-hexene, and has no discernable crystallization according to DSC using ASTM 3418-97; and
the hydrogenated oligomer composition is characterized by:
a 100° C. kinematic viscosity in a range from 85 to 115 cSt;
a viscosity index in a range from 155 to 165; and
a pour point in a range from −25 to −35° C.

3. The base oil or lubricant composition of claim 1, wherein the base oil or lubricant composition has:
a 100° C. kinematic viscosity in a range from 35 to 45 cSt;
a viscosity index in a range from 130 to 180; and
a pour point of less than −32° C.

4. The base oil or lubricant composition of claim 1, wherein the base oil or lubricant composition has:
a 100° C. kinematic viscosity in a range from 37 to 43 cSt;
a viscosity index in a range from 140 to 165; and
a pour point in a range from −30 to −50° C.

5. The base oil or lubricant composition of claim 1, wherein:
the base oil or lubricant composition has a 40° C. kinematic viscosity in a range from 375 to 425 cSt; and
the weight ratio of the hydrogenated oligomer composition:low viscosity PAO is in a range from 35:65 to 80:20.

6. The base oil or lubricant composition of claim 1, wherein the low viscosity PAO has:
a 100° C. kinematic viscosity in a range from 1 to 15 cSt;
a viscosity index in a range from 90 to 200; and
a pour point in a range from −23 to −80° C.

7. The base oil or lubricant composition of claim 1, wherein the low viscosity PAO comprises monomer units derived from a $C_6$ to $C_{18}$ normal alpha olefin.

8. The base oil or lubricant composition of claim 1, wherein the base oil or lubricant composition comprises less than 10 wt. % of a PAO comprising at least 80 wt. % of monomer units derived from 1-decene.

9. A base oil or lubricant composition comprising:
(i) a hydrogenated oligomer composition comprising at least 80 wt. % monomer units derived from 1-hexene, and characterized by a 100° C. kinematic viscosity in a range from 75 to 150 cSt, a viscosity index in a range from 150 to 180, and a pour point in a range from −20 to −40° C.; and
(ii) a high viscosity PAO having a 100° C. kinematic viscosity in a range from 75 to 150 cSt;
wherein a weight ratio of the hydrogenated oligomer composition:high viscosity PAO is in a range from 25:75 to 80:20; and
wherein the base oil or lubricant composition has a 100° C. kinematic viscosity in a range from 80 to 120 cSt.

10. The base oil or lubricant composition of claim 9, wherein:
the hydrogenated oligomer composition comprises at least 95 wt. % monomer units derived from 1-hexene, and has no discernable crystallization according to DSC using ASTM 3418-97; and
the hydrogenated oligomer composition is characterized by:
a 100° C. kinematic viscosity in a range from 80 to 125 cSt;
a viscosity index in a range from 150 to 170; and
a pour point in a range from −25 to −40° C.

11. The base oil or lubricant composition of claim 9, wherein the base oil or lubricant composition has:
a 100° C. kinematic viscosity in a range from 85 to 115 cSt;
a viscosity index in a range from 160 to 190; and
a pour point of less than −25° C.

12. The base oil or lubricant composition of claim 9, wherein the base oil or lubricant composition has:
a 100° C. kinematic viscosity in a range from 90 to 110 cSt;
a viscosity index in a range from 165 to 180; and
a pour point in a range from −28 to −38° C.

13. The base oil or lubricant composition of claim 9, wherein:
the base oil or lubricant composition has a 40° C. kinematic viscosity in a range from 1100 to 1300 cSt; and
the weight ratio of the hydrogenated oligomer composition:high viscosity PAO is in a range from 40:60 to 60:40.

14. The base oil or lubricant composition of claim 9, wherein the high viscosity PAO has:
a 100° C. kinematic viscosity in a range from 85 to 115 cSt;
a viscosity index in a range from 155 to 250; and
a pour point in a range from −26 to −50° C.

15. The base oil or lubricant composition of claim 9, wherein the high viscosity PAO comprises monomer units derived from a $C_8$ to $C_{18}$ normal alpha olefin.

16. The base oil or lubricant composition of claim 9, wherein the base oil or lubricant composition comprises less than 5 wt. % of a PAO comprising at least 95 wt. % of monomer units derived from 1-decene.

* * * * *